US012716050B2

(12) United States Patent
Yue et al.

(10) Patent No.: US 12,716,050 B2
(45) Date of Patent: Aug. 25, 2026

(54) TWO METHODS FOR PREPARING UNIVERSAL MICROBIAL MEDIUM BY EUTECTIC SYSTEM-BASED CELLULOSE LIQUEFACTION

(71) Applicant: Xinjiang University, Urumqi (CN)

(72) Inventors: Haitao Yue, Urumqi (CN); Jieyi Wu, Urumqi (CN); Duo Yang, Urumqi (CN); Na Wu, Urumqi (CN); Luyu Zhao, Urumqi (CN); Xiangxiang Xing, Urumqi (CN)

(73) Assignee: XINJIANG UNIVERSITY, Urumqi (CN)

( * ) Notice: Subject to any disclaimer, the term of this patent is extended or adjusted under 35 U.S.C. 154(b) by 904 days.

(21) Appl. No.: 17/831,088

(22) Filed: Jun. 2, 2022

(65) Prior Publication Data

US 2022/0396763 A1 Dec. 15, 2022

(30) Foreign Application Priority Data

Jun. 10, 2021 (CN) ........................ 202110649976.1

(51) Int. Cl.
*C12N 1/22* (2006.01)
*C08B 1/00* (2006.01)
*C12N 1/20* (2026.01)

(52) U.S. Cl.
CPC ................ *C12N 1/22* (2013.01); *C08B 1/003* (2013.01); *C12N 1/20* (2013.01)

(58) Field of Classification Search
CPC .. C08B 1/003; C12N 1/22; C12N 1/20; C12N 1/38; C12R 2001/01; C12R 2001/07; C12R 2001/13; C12R 2001/19; C12R 2001/265
See application file for complete search history.

(56) References Cited

U.S. PATENT DOCUMENTS 7,959,765 B2 * 6/2011 Argyropoulos ......... C10B 53/02 585/242
9,394,375 B2 * 7/2016 Daly ........................ C08H 8/00
2010/0196967 A1 * 8/2010 Edye ......................... C12P 7/10 435/165
2013/0233501 A1 * 9/2013 Van Zyl ............... C09D 105/14 435/274
2014/0004563 A1 * 1/2014 Paripati ..................... F26B 3/34 435/68.1
2020/0239508 A1 * 7/2020 Uroos .................... B01D 37/00
2021/0079593 A1 * 3/2021 Abidi ...................... C08B 1/003
2021/0145908 A1 * 5/2021 Lapidot ................... A23L 33/10

FOREIGN PATENT DOCUMENTS

CN 101007867 A * 8/2007 ............. B29C 48/40

OTHER PUBLICATIONS

English Translation of CN 101007867 A (Year: 2007).*

* cited by examiner

*Primary Examiner* — Anthony J Zimmer
*Assistant Examiner* — Abdul-Rahman Yusuf Waleed Smari
(74) *Attorney, Agent, or Firm* — Scully, Scott, Murphy & Presser, P.C.

(57) ABSTRACT

A method for preparing a universal microbial medium by eutectic system-based cellulose liquefaction. The method includes: 1) mixing ionic liquid and cellulose, where the ionic liquid is preheated; 2) mixing a mixed solution I obtained in step 1) and distilled water; 3) filtering a mixed solution II obtained in step 2); and 4) diluting a filtrate obtained in step 3) with the distilled water to obtain the carbon source. A medium prepared from the carbon source can be used for culturing various microorganisms, with a desirable growth state of the microorganisms.

7 Claims, 12 Drawing Sheets

TWO METHODS FOR PREPARING UNIVERSAL MICROBIAL MEDIUM BY EUTECTIC SYSTEM-BASED CELLULOSE LIQUEFACTION

CROSS REFERENCE TO RELATED APPLICATION

This patent application claims the benefit and priority of Chinese Patent Application No. 202110649976.1, filed on Jun. 10, 2021, the content of which is incorporated by reference herein in its entirety as part of the present application.

TECHNICAL FIELD

The present disclosure relates to the field of microbiology, and more particularly, it relates to a method for preparing a universal microbial medium by eutectic system-based cellulose liquefaction. Specifically, the present disclosure relates to a carbon source, a method for preparing a carbon source, a novel microbial medium, and a method for culturing microorganisms.

BACKGROUND ART

A medium is a main place for growth and metabolism of microorganisms. The medium used in industrial production is generally called a fermentation medium or an industrial medium. Basic components of the medium generally include a carbon source, a nitrogen source, inorganic salts, water and growth factors. The carbon source, as a nutrient source that meets carbon elements required for the growth and reproduction of microorganisms, is basic component for microbial growth. There are many carbon sources that can be utilized by microorganisms. The carbon source in the industrial medium is selected based on growth characteristics and production requirements of the microorganisms, while considering economic benefits and environmental protection requirements of the industrial medium in large-scale production. In recent years, with the continuous upgrading of environmental protection industries and the continuous introduction of policies, comprehensive utilization of agricultural wastes has been continuously strengthened. It is a strategy that meets both economic effects and environmental requirements by using cellulose-rich straw as a carbon source for industrial media.

Most of the carbon sources used in industry are mainly carbohydrates, and can be divided into fast-acting carbon sources and delayed-acting carbon sources according to a priority of utilization. Generally, the fast-acting carbon sources are glucose, while the delayed-acting carbon sources are most grain products and starch-rich substances such as cornstarch, bran, and potatoes. Cellulose, compared to these carbohydrates commonly used in fermentation industries, cannot be utilized by most industrial strains, and only some strains with cellulose degradation pathways can degrade the cellulose into monosaccharides for utilization. However, since in large-scale liquid shake flask fermentation, it is difficult for the cellulose to form a stable solution in aqueous and organic phases, even the strains with cellulose degradation pathways are difficult to proliferate in liquid shake flasks. The cellulose has obvious advantages. As the oldest and most abundant natural polymer compound on the earth, the cellulose can be easily obtained and is the most precious natural renewable resource for human beings. Hemp, wheat straw, rice straw, bagasse and other agricultural wastes are rich sources of the cellulose. At present, many developed countries are strengthening the utilization of cellulose in these agricultural wastes in consideration of economic benefits and environmental protection requirements; some countries and regions have formed a complete industry chain, and the cellulose is widely used in bioethanol production, papermaking, and plastic processing. In addition, compared with glucose, starch and other common industrial carbohydrates, the cellulose has a low cost; and a large amount of the cellulose is produced in agricultural production annually. Therefore, making full use of the cellulose as a cheap carbon source for industrial medium will make a great contribution to global sustainable development.

Natural cellulose has high crystallinity, regular cellulose structure, and dense crystal structure. The alcoholic hydroxyl groups in macromolecular glucosyl rings will form hydrogen bonds with extremely strong bond energy, making the cellulose insoluble in water and other conventional organic solvents, and only soluble in alkaline or high-concentration inorganic acid solutions. Accordingly, many industrial microorganisms cannot utilize the cellulose for production. The cellulose, due to relatively stable chemical properties, can be oxidized, esterified and etherified under certain conditions, and can also be degraded by acids and enzymes to a certain extent. It is a key factor for the cellulose to be utilized by many microorganisms through destruction of cellulose structure via effective pretreatments. In the 1960s, people tried to use PF/DMSO as a desirable solvent for the cellulose due to a particularly strong dissolving power. However, the PF/DMSO, due to toxicity and difficulty in recovery, is not conducive to environmental protection. In a NaOH/$CS_2$ system, a certain amount of $CS_2$ is introduced into alkali-treated cellulose to form cellulose xanthate soluble in sodium hydroxide. However, the dissolving system has a cumbersome process and great environmental pollution. In addition, a protonic acid system is also a method for dissolving the cellulose, which is generally used to produce cellulose derivatives. However, development of the system is limited due to easy generation of toxic residues such as $CS_2$ and ammonia during the production, seriously polluting the environment. Furthermore, a carbamate system is to produce carbamate by mixing urea with NaOH-treated cellulose and adding an inert solvent. Although being relatively environmental-friendly, the method cannot be widely used due to a complicated process and impurities generation. In recent years, N-methylmorpholine aqueous solution (NMMO·$H_2O$) is the most representative organic solvent, which has a relatively high dissolution efficiency and no degradation. However, the NMMO has a high cost and cannot be directly applied to industrial production.

Therefore, it is urgent to explore and optimize a more convenient, efficient and environmental-friendly method for treating cellulose to conduct microbial culture, thereby making the cellulose more widely used.

SUMMARY

The present disclosure has been disclosed based on discovery and recognition of the following problems:

Cellulose can be liquefied by a solution system of ionic liquid (IL) and sodium hydroxide (NaOH)/urea (Urea), and liquefied cellulose can be widely used in industrial production. The liquefied cellulose is fractionated. It is surprisingly found that a novel broad-spectrum medium can be constructed from fractionated cellulose liquid, and the ionic liquid can be efficiently recycled under reasonable conditions.

Therefore, a first aspect of the present disclosure is to provide a method for preparing a carbon source. The method includes: 1) mixing ionic liquid and cellulose, where the ionic liquid is preheated; 2) mixing a mixed solution I obtained in step 1) and distilled water; 3) filtering a mixed solution II obtained in step 2); and 4) diluting a filtrate I obtained in step 3) with the distilled water to obtain the carbon source. Compared with co-heating the ionic liquid and the cellulose directly, preheating the ionic liquid can dissolve the cellulose more fully in the obtained carbon source. A medium prepared by the carbon source obtained by the method is used for microbial culture, and cultured strains can be proliferated with a desirable growth state.

The method may further include at least one of the following additional technical features:

In an example, the ionic liquid may preheated at 70° C. to 90° C. The ionic liquid can be completely melted after preheating at 70° C. to 90° C.

In an example, the ionic liquid and the cellulose may be mixed in a mass ratio of 5:3 to 10:1. With the mass ratio, the ionic liquid can completely dissolve the cellulose, and an obtained mixed system is in a liquid state without viscous or flaky cellulose.

In an example, the mixed solution I obtained in step 1) and the distilled water may be mixed in a volume ratio of 1:2.

In an example, the method may further include: conducting fractionation on a diluted product obtained in step 4) to obtain a carbon source without the ionic liquid and first recycled ionic liquid. Fractionation allows separation of the carbon source and the toxic ionic liquid, and the proliferation of microorganisms is accelerated in the medium prepared from the carbon source without ionic liquid.

In an example, the ionic liquid may include 1-butyl-3-methylimidazolium chloride. Compared to ionic liquids 1-butyl-3-methylimidazolium borate, 1-allyl-3-methylimidazolium chloride, and 1-butyl-3-methylimidazolium acetate, the 1-butyl-3-methylimidazolium chloride dissolves cellulose more completely, with a significantly shortened dissolution time.

In an example, the ionic liquid and the cellulose may be mixed specifically by: 1) stirring the ionic liquid and a cellulose mixed solution at 100° C. to 140° C.; 2) stirring a resulting mixed solution at 150° C. to 200° C.; and 3) repeating step 2) three times. Heating at the above temperature with continuous stirring greatly shortens the dissolution time of cellulose and improves the dissolving efficiency.

In an example, the diluting may be conducted according to a ratio of a mass of the ionic liquid to a diluting volume at 1 g:60 mL to 1 g:30 mL. With the above ratio, when the medium is prepared using the ionic liquid-containing carbon source, the ionic liquid in the medium has a low concentration, and the microorganisms can proliferate normally with a desirable growth state.

In an example, the diluting may be conducted according to the ratio of the mass of the ionic liquid to the diluting volume at 1 g:50 mL. With the above ratio, when the medium is prepared using the ionic liquid-containing carbon source, an ionic liquid concentration and a carbon source concentration in the medium each meet growth requirements of the microorganisms, and the microorganisms can proliferate normally with a desirable growth state.

In an example, the diluting may be conducted according to a ratio of a mass of the cellulose and a diluting volume at 1 g:50 mL to 1 g:30 mL.

In an example, the diluting may be conducted according to the ratio of the mass of the cellulose and the diluting volume at 1 g:40 mL. When the diluting is conducted according to the ratio of the mass of the cellulose and the diluting volume at 1 g:40 mL, when the medium is prepared by using the carbon source without ionic liquid, the medium has an optimum carbon source concentration, and the microorganism have a desirable growth state.

In an example, the method may further include the following steps: 1) mixing the first recycled ionic liquid with the cellulose at a mass ratio of 5:3 to 10:1, where the first recycled ionic liquid is preheated at 100° C. to 140° C.; 2) stirring a mixture I obtained in step 1) at 150° C. to 200° C.; 3) repeating step 2) two times; 4) mixing a mixture II obtained in step 3) and the distilled water in a volume ratio of 1:2; 5) filtering a product A obtained in step 4); 6) diluting a filtrate A obtained in step 5) with the distilled water; and 7) conducting fractionation on a diluted product A obtained in step 6) to obtain the carbon source and second recycled ionic liquid. The first recycled ionic liquid can still completely dissolve the cellulose in microwave heating at 100° C. to 140° C. and 150° C. to 200° C., and the mixed system is in a liquid state without viscous or flaky cellulose.

In an example, the fractionation may be conducted at a vacuum pressure of −0.070 Mpa to −0.095 Mpa and 40 rpm to 70 rpm, in a water bath at 20° C. to 50° C. and then 55° C. to 80° C. The fractionation can well separate the ionic liquid from the carbon source, and the obtained carbon source does not contain the ionic liquid.

A second aspect of the present disclosure is to provide a carbon source. The carbon source is obtained by the methods described in the first and second aspects. The microorganisms cultured in the medium prepared by using the carbon source can proliferate and grow well.

A third aspect of the present disclosure is to provide a method for preparing a medium. In an example, the method includes: adding $NH_4Cl$, $MgSO_4$, and NaCl to the carbon source in the second aspect, such that the $NH_4Cl$ has a final concentration of 2 g/L, the $MgSO_4$ has a final concentration of 0.2 g/L, and the NaCl has a final concentration of 10 g/L. The microorganisms cultured in the medium obtained by the method and the ratio have a desirable growth state.

A fourth aspect of the present disclosure is to provide a medium. The medium is obtained by the method in the third aspect. The microorganisms cultured by the medium can proliferate and grow well.

A fifth aspect of the present disclosure is to provide a method for culturing microorganisms, including: culturing the microorganisms in the medium in the fourth aspect. The method can culture various microorganisms, and the microorganisms can proliferate and grow well.

The method may further include at least one of the following additional technical features:

In an example, the culturing may be conducted at 37° C. and 150 rpm. The medium in the fourth aspect can culture various microorganisms at 37° C. and 150 rpm, and the microorganisms can proliferate and grow well.

In an example, the microorganisms may include at least one of *Brevibacterium casei, Bacillus, Micrococcus luteus, Enterobacter cloacae, Halomonas*, and *Escherichia coli*. There is no special limitation on types of microorganisms that can be cultured by the method, and microorganisms that can be propagated in the medium in the fourth aspect at 37° C. and 150 rpm can be cultured by the method.

A sixth aspect of the present disclosure is to provide a method for preparing a carbon source. The method includes the following steps: 1) mixing an alkaline mixed solution I and cellulose in a volume-to-mass ratio of 50 mL:1 g to 200 mL:1 g to obtain an alkaline mixed solution II, where the alkaline mixed solution I includes sodium hydroxide and urea; 2) freezing the alkaline mixed solution II at −10° C. to −80° C. for 24 h; 3) heating the frozen alkaline mixed solution II; 4) subjecting the alkaline mixed solution II heated to 0° C. to −20° C. to pH adjustment to obtain an alkaline mixed solution III; and 5) filtering the alkaline mixed solution III adjusted to a pH value of 7 to 11 to obtain a filtrate that forms the carbon source. The carbon source obtained by the method can be prepared into a medium to culture various microorganisms that grow well.

The method may further include at least one of the following additional technical features:

In an example, the alkaline mixed solution I may include the sodium hydroxide with the mass ratio of 3% to 8% and the urea with the mass ratio of 6% to 14%.

In an example, the alkaline mixed solution I may include the sodium hydroxide with the mass ratio of 3% to 5% and the urea with the mass ratio of 6% to 10%. With the above ratio of the sodium hydroxide and the urea, the cellulose can be more fully dissolved.

In an example, the alkaline mixed solution I may include the sodium hydroxide with the mass ratio of 4% and the urea with the mass ratio of 7%. With the above ratio of the sodium hydroxide and the urea, an obtained NaOH/Urea-microcrystalline cellulose solution in the form of ice water is gradually clarified after stirring, and the cellulose is completely dissolved.

The cellulose in the first and sixth aspects is solid cellulose. There is no special limitation on the solid cellulose, and the solid cellulose can be purified cellulose or a mixture.

In an example, the cellulose may be microcrystalline cellulose. There is no special limitation on the microcrystalline cellulose, and all linear polysaccharides bound by a β-1,4-glucosidic bond can be used.

In an example, the cellulose may be agricultural waste straw. There is no special limitation on a type of the cellulose, and any agricultural waste straw containing the cellulose can be used to produce the carbon source and the medium in the first and sixth aspects, such as: licorice, wheat, corn, sorghum, cotton, rice straw and waste apple trees, peach trees and other substances containing cellulose.

In an example, the cellulose may be at least one of licorice straw, wheat straw, corn straw, sorghum straw, and cotton straw. The pH adjustment may be conducted using a dilute acid.

In an example, the dilute acid may be HCl.

A seventh aspect of the present disclosure is to provide a carbon source. The carbon source is obtained by the method in the fifth aspect. The microorganisms cultured in a novel broad-spectrum medium prepared by the carbon source grow well.

An eighth aspect of the present disclosure is to provide a method for preparing a medium. In an example, the method includes: adding $NH_4Cl$, $MgSO_4$, and NaCl to the carbon source in the seventh aspect, such that the $NH_4Cl$ has a final concentration of 2 g/L, the $MgSO_4$ has a final concentration of 0.2 g/L, and the NaCl has a final concentration of 10 g/L. The microorganisms cultured in the medium obtained by the method have a desirable growth state.

A ninth aspect of the present disclosure is to provide a medium. The medium is obtained by the method in the eighth aspect. The microorganisms cultured in the medium have a desirable growth state.

A tenth aspect of the present disclosure is to provide a method for culturing microorganisms, including: culturing the microorganisms in the medium according to the present disclosure. The method can culture various microorganisms, and the microorganisms can proliferate and grow well, inoculated strains can accumulate PHA in the medium.

In an example, the culturing may be conducted at 35° C. to 37° C. and 145 rpm to 155 rpm. The medium in the ninth aspect can culture various microorganisms at 37° C. and 150 rpm, and the microorganisms can proliferate and grow well.

In an example, the microorganisms may be saline-alkali-tolerant strains. There is no special limitation on types of microorganisms that can be cultured by the method, and all saline-alkali-tolerant strains can be cultured by the method.

In an example, the microorganisms may include at least one of *Brevibacterium casei, Bacillus, Micrococcus luteus, Enterobacter cloacae, Halomonas*, and *Escherichia coli*. The *Brevibacterium casei, Bacillus, Micrococcus luteus, Enterobacter cloacae, Halomonas*, and *Escherichia coli* can all grow and proliferate.

Additional aspects and advantages of the present disclosure will be partly provided in the following description, and partly become evident in the following description or are understood through the practice of the present disclosure.

BRIEF DESCRIPTION OF THE DRAWINGS

FIG. 11A shows a chromatographic result of a chloroform sample, where a first chromatographic peak is a chloroform solution with a retention time of 2.658 min; FIG. 11B shows a chromatographic result of a PHA standard sample after esterification, where a first chromatographic peak is 3HB with a retention time of 2.284 min, and a second chromatographic peak is chloroform with a retention time of 2.681 min; and FIG. 11C shows a chromatographic result of a freeze-dried strain of *Micrococcus luteus* after esterification, where a first peak has a retention time of 2.287 min, which is basically the same as that of a standard 3HB, and the chromatographic peak is intracellular 3HB of the *Micrococcus luteus.*

DETAILED DESCRIPTION OF THE EMBODIMENTS

Figure 1:
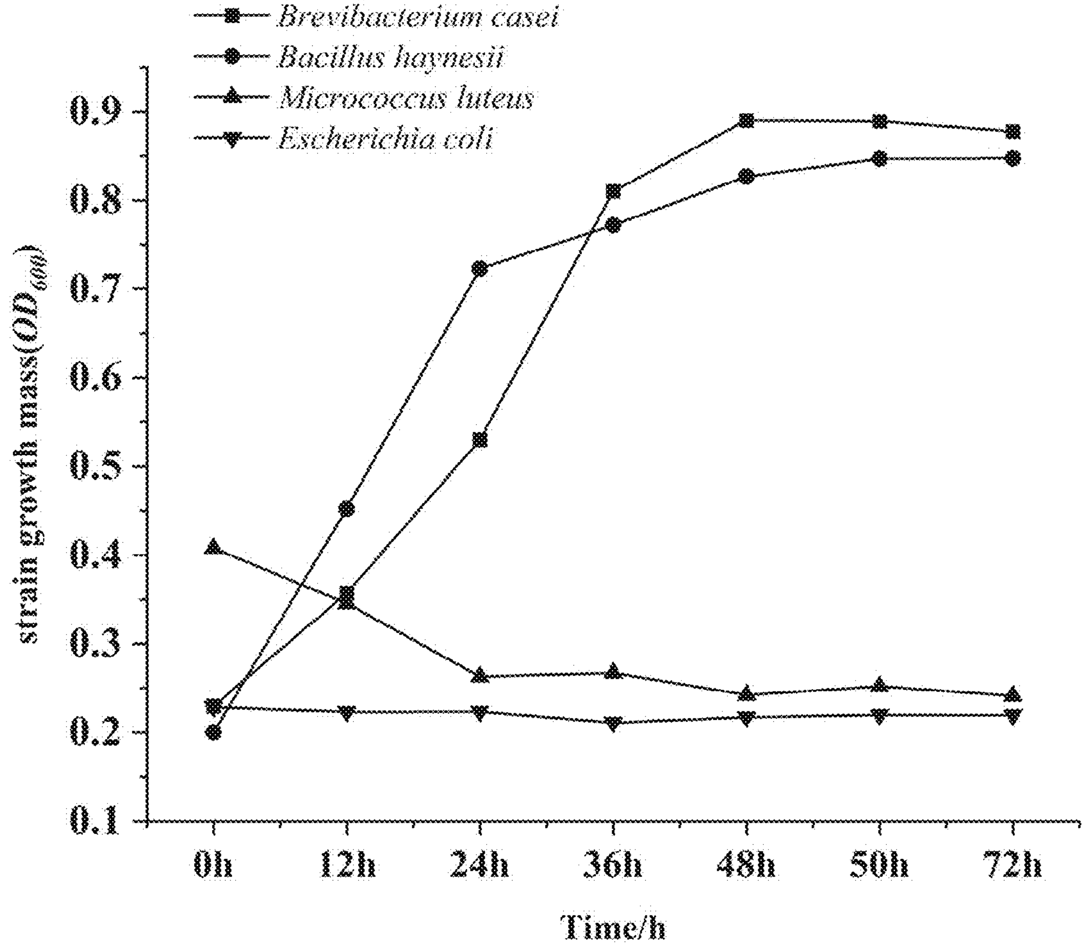
FIG. 1 shows a growth curve diagram of *Brevibacterium casei, Bacillus, Micrococcus luteus, Enterobacter cloacae, Halomonas*, and *Escherichia coli* in a medium with liquid cellulose as a carbon source in an example of the present disclosure.

The embodiments of the present disclosure are described in detail below, examples of which are shown in the accompanying drawings. The embodiments described below with reference to the drawings are illustrative, which are merely intended to explain the present disclosure, rather than to limit the present disclosure.

Moreover, the terms such as "first" and "second" are used only for the purpose of description and should not be construed as indicating or implying a relative importance, or implicitly indicating a quantity of indicated technical features. Therefore, features defined by "first" and "second" may explicitly or implicitly include at least one of the features. In description of the present disclosure, "a plurality of" means at least two, for example, two or three, unless otherwise clearly and specifically limited.

Microcrystalline cellulose is a purified, partially-depolymerized cellulose, which is a white, odorless, and tasteless crystalline powder composed of porous microparticles, and uses linear polysaccharides bound by a β-1,4-glucosidic bond as a main component. The microcrystalline cellulose has a degree of polymerization of about 3,000 to 10,000 glucose molecules. In general plant fibers, microcrystalline cellulose accounts for about 73%, and the other 30% is amorphous cellulose.

A purpose of the present disclosure is to pretreat cellulose through ionic liquid and a NaOH/Urea solution system for liquefication, and to construct a novel broad-spectrum medium using liquefied cellulose as a carbon source and recover the ionic liquid. Ionic liquid for pretreating cellulose, a concentration of the ionic liquid, an addition ratio of the ionic liquid to the cellulose, and a temperature at which the ionic liquid decomposes the cellulose are screened to obtain optimum experimental conditions for the ionic liquid to dissolve the cellulose. Meanwhile, a concentration of NaOH and Urea, an addition ratio of a NaOH/Urea solution to the cellulose, and a temperature of NaOH/Urea solution pretreatment of the cellulose in a NaOH/Urea solution system are screened to obtain optimum experimental conditions for pretreatment of the cellulose with NaOH/Urea solution. The carbon source obtained under the optimal cellulose dissolving conditions is diluted in a certain number of times, the carbon source is used to prepare a broad-spectrum microbial medium, and a culture ability of the broad-spectrum medium is verified.

The method provided by the present disclosure includes the following steps:

(1) The cellulose is pretreated by the ionic liquid, and filtered and diluted; a novel medium is constructed using diluted mixed liquid as a carbon source for culturing bacteria, or the cellulose is pretreated by the ionic liquid, and subjected to filtration, dilution, and fractionation; the ionic liquid in an evaporating flask of a rotary evaporator is recovered, and a novel medium is constructed using colorless and transparent liquid in the evaporating flask of the rotary evaporator as a carbon source for culturing bacteria; the above steps are continued with the recovered ionic liquid.

(2) The cellulose is pretreated using a NaOH/Urea solution system, followed by freezing, thawing, stirring, pH adjustment, and filtration; a novel medium is constructed using a filtrate as a carbon source for culturing bacteria.

To prepare a medium with ionic liquid-pretreated cellulose as a carbon source and recycle ionic liquid, the present disclosure adopts the following technical solutions.

(1) The ionic liquid is heated to 70° C. to 90° C., mixed with the cellulose in a mass ratio of 5:3 to 10:1, heated to 100° C. to 140° C., stopped heating, and stirred. A mixture is heated to 150° C. to 200° C., stop heating, and stirred (repeating 3 times). 2 times volume of distilled water is added to a beaker, and stirred, the mixture is dissolved and filtered with a fast qualitative filter paper. The distilled water is added to dilute the filtrate, with a dilution ratio of a dilution volume and a dissolved cellulose mass of 1 mL:50 g to 1 mL:30 g, or 1 mL:60 g to 1 mL:30 g; when mixed liquid after dilution is not fractionated to be used as a carbon source to construct a medium, the obtained mixed liquid is a carbon source containing a large amount of the ionic liquid, and the ionic liquid is toxic. Therefore, to ensure the normal growth of microorganisms, it is necessary to dilute the ionic liquid in the mixed liquid. A dilution ratio is a ratio of a mass of the added ionic liquid and a dilution volume of 1 g:60 mL to 1 g:30 mL; in the mixed liquid after dilution, $NH_4Cl$ (2 g/L), $MgSO_4$ (0.2 g/L), and NaCl (10 g/L) are added in proportion, followed by sterilization through autoclaving at 115° C. for 15 min. The strain is inoculated, changes of $OD_{600}$ are observed at 37° C., 150 rpm. When the mixed liquid after dilution is fractionated, the mixed liquid obtained after fractionation is a carbon source without the ionic liquid; to ensure the growth of microorganisms, the concentration of the carbon source in the medium should be guaranteed. A dilution ratio is a ratio of a mass of the dissolved cellulose and a dilution volume of 1 g:50 mL to 1 g:30 mL.

(2) Fractionation is conducted on the mixed solution obtained in step (1) after dilution, where a vacuum pressure is −0.070 Mpa to −0.095 Mpa, a first water bath temperature is 20° C. to 50° C., a second water bath temperature is 55° C. to 80° C., that is, the boiling point changes once, and a rotation speed is 50 rpm; after the fractionation, a colorless and transparent liquid can be obtained in a collection bottle, which is a carbon source without the ionic liquid; and ionic liquid is recovered in an evaporation bottle, and the ionic liquid can be recovered multiple times.

(3) in the carbon source without ionic liquid obtained in step 2) or the carbon source with ionic liquid obtained in step 1), $NH_4Cl$ (2 g/L), $MgSO_4$ (0.2 g/L), and NaCl (10 g/L) are added in proportion, followed by conducting autoclaving at 115° C. for 15 min. The strain is inoculated, changes of $OD_{600}$ are observed at 37° C., 150 rpm.

(4) The ionic liquid recovered in step (2) is heated to 100° C. to 130° C., followed by stopping heating; a resulting product was mixed with cellulose according to a mass ratio of 5:3 to 10:1, and heated to 140° C. to 180° C., followed by stopping heating; and a resulting product was stirred (repeating 3 times). 2 times volume of distilled water is added to a beaker, and stirred, the mixture is dissolved and filtered with a fast qualitative filter paper. The distilled water was added to dilute the filtrate at a ratio of constant volume and dissolved mass of 1 mL:30 g to 1 mL:60 g.

(5) Fractionation is conducted on the mixed solution obtained in step (4) after dilution, where a vacuum pressure is −0.070 Mpa to −0.095 Mpa, a first water bath temperature is 20° C. to 50° C., a second water bath temperature is 55° C. to 80° C., that is, the boiling point changes once, and a rotation speed is 50 rpm; after the fractionation, a colorless and transparent liquid can be obtained in the collection bottle; and ionic liquid is recovered in the evaporation bottle.

(6) in the solution in the collection bottle, $NH_4Cl$ (2 g/L), $MgSO_4$ (0.2 g/L), and NaCl (10 g/L) are added in proportion, followed by conducting autoclaving at 110° C. for 15 min. The strain is inoculated, changes of $OD_{600}$ are observed at 37° C., 150 rpm.

(7) The ionic liquid recovered in step (5) is heated to 100° C. to 130° C., followed by stopping heating; a resulting product was mixed with cellulose according to a mass ratio of 5:3 to 10:1, and heated to 140° C. to 180° C., followed by stopping heating; and a resulting product was stirred (repeating 3 times). 2 times volume of distilled water is added to a beaker, and stirred, the mixture is dissolved and filtered with a fast qualitative filter paper. The distilled water was added to dilute the filtrate at a ratio of constant volume and dissolved mass of 1 mL:30 g to 1 mL: 60 g.

(8) Fractionation is conducted on the mixed solution obtained in step (7) after dilution, where a vacuum pressure is −0.070 Mpa to −0.095 Mpa, a first water bath temperature is 20° C. to 50° C., a second water bath temperature is 55° C. to 80° C., that is, the boiling point changes once, and a rotation speed is 50 rpm; after the fractionation, a colorless and transparent liquid can be obtained in the collection bottle; and ionic liquid is recovered in the evaporation bottle.

(9) in the solution in the collection bottle, $NH_4Cl$ (2 g/L), $MgSO_4$ (0.2 g/L), and NaCl (10 g/L) are added in proportion, followed by conducting autoclaving at 115° C. for 15 min. The strain is inoculated, changes of $OD_{600}$ are observed at 37° C., 150 rpm.

To prepare a medium with NaOH/Urea solution system-pretreated cellulose as a carbon source, the present disclosure adopts the following technical solutions.

(1) NaOH (3% to 8%) and Urea (6% to 14%) are mixed and diluted to 1000 ml, mixed with 5 g to 20 g of cellulose, and pre-frozen at −10° C. to −80° C. for 24 h.

(2) A pre-frozen solution obtained in step (1) was placed at room temperature, heated to 0° C. to −40° C. to form an ice-water mixed state, and stirred until the solution is completely dissolved; after adjusting a pH value to 7 to 11 with HCl, the solution is filtered with gauze to collect a filtrate.

(3) in the filtrate, $NH_4Cl$ (2 g/L), $MgSO_4$ (0.2 g/L), and NaCl (10 g/L) are added in proportion, followed by conducting autoclaving at 115° C. for 15 min; *Micrococcus luteus* was inoculated, and changes of CDW are observed at 37° C., 150 rpm.

(4) After 72 h, a culture was transferred to a 50 mL centrifuge tube, centrifuged at 12,000 rpm for 10 min, and a supernatant was discarded; a resulting precipitate was pre-frozen at −70° C. for 4 h, and then lyophilized overnight in a −60° C. vacuum lyophilizer.

(5) About 20 mg of freeze-dried cell samples were accurately weighed (0.0001) and placed in an esterification tube, and 2 mL of chloroform (AR) and 2 mL of an esterification solution (including 500 ml/L anhydrous methanol+1 g/L benzoic acid+3% (v/v) concentrated sulfuric acid) were added. About 10 mg of a standard PHA sample (PHB) was treated in the same way to prepare a chloroform solution of the standard sample. The esterification tube is sealed, shaken to mix evenly, followed by conducting esterification at a constant temperature of 100° C. for 4 h. After cooling to room temperature, 1 mL of $ddH_2O$ was added, shaken until completely mixed, and allowed to stand for about 30 min for layering. After the aqueous phase and the organic phase are completely separated, a lower layer solution (chloroform phase) was subjected to GC analysis to calculate a 3HB content.

Experiments have proved that, in the present disclosure, a novel medium that can make multiple strains of bacteria of different species proliferate is constructed using ionic liquid-pretreated cellulose as a carbon source; meanwhile, the recovered ionic liquid maintains certain original properties. In addition, a novel medium that can make some bacteria proliferate while accumulating PHA is constructed using the NaOH/Urea solution system-pretreated cellulose as a carbon source.

The materials, reagents, and the like used in the following examples are all commercially available, unless otherwise specified.

The ionic liquid is purchased from Shanghai Chengjie Chemical Co., Ltd.; the rotary evaporator is purchased from Shanghai Yarong Biochemical Instrument Factory; a rapid qualitative filter paper is purchased from Hangzhou Special Paper Co., Ltd.; a gas chromatograph model is Agilent Technologies 6850, purchased from Agilent Technologies (China) Co., Ltd.; a Chinese herbal medicine grinder is purchased from Tianjin Taiste Instrument Co., Ltd.; $NH_4Cl$, $MgSO_4$, NaCl, Urea are purchased from Tianjin Beilian Chemcp Co., Ltd.; NaOH, hydrochloric acid, anhydrous methanol, chloroform and concentrated sulfuric acid are purchased from Tianjin Yongsheng Fine Chemical Co., Ltd.; peptone, yeast powder and agar are purchased from Beijing Aubox Biotechnology Co., Ltd.; *Escherichia coli* is purchased from Sangon Biotech (Shanghai) Co., Ltd.; *Brevibacterium casei, Bacillus, Micrococcus luteus, Enterobacter cloacae, Halomonas*, and *Bacillus licheniformis* are provided by the Yue Haitao experimental group of Xinjiang University; and media are prepared with distilled water unless otherwise specified.

The present disclosure is described below with reference to the specific examples. It should be noted that these examples are only illustrative and do not limit the present disclosure in any way.

Example 1 Screening of Ionic Solutions

Different ionic liquids (1-butyl-3-methylimidazolium chloride, 1-butyl-3-methylimidazolium borate, 1-allyl-3-methylimidazolium chloride, and 1-butyl-3-methylimidazole acetate) pretreating cellulose were selected, to screen ionic liquid that can dissolve the cellulose efficiently, and the experimental conditions were roughly selected at the same time. The treatment methods included: 1) ionic liquid was heated in a water bath, mixed with the cellulose in proportion, followed by continuing water bath or microwave heating, where a temperature of the preheated ionic liquid was the same as that at which the two were continued to be heated after mixing; 2) the ionic liquid and the cellulose were mixed in proportion, heated, a degree of cellulose dissolution was observed, and a cellulose dissolution time was recorded. The specific experimental phenomena and experimental conclusions were shown in Table 1. After preheating to a liquid state at 110° C., the 1-butyl-3-methylimidazolium chloride was mixed with the cellulose in a mass ratio of 5:3, continued to partially dissolve; the IL turned brown and smelled like caramel, and 100 mL of water was added to let stand for stratification; it was considered that the ionic liquid could well process the cellulose under the above experimental conditions. However, other ionic liquids had a poor effect in pretreatment of cellulose, or the ionic liquid and the cellulose had a relatively large dissolving mass ratio and a long dissolution time, which were not recommended to use.

TABLE 1

| No. | Types of ionic solutions | Ionic solution/g | Microcrystalline cellulose/g | Experimental temperature | Treatment | Dissolution time | Dissolved state | Conclusion |
|---|---|---|---|---|---|---|---|---|
| 1 | 1-butyl-3-methylimidazolium chloride | 10 | 1 | 90° C. | IL and microcrystalline cellulose are co-heated, stirred for 20 sec every 5 min | 40 min | Microcrystalline cellulose dissolves, but newly-added microcrystalline cellulose has increased viscosity and the cellulose does not dissolve | Microcrystalline cellulose has a desirable dissolution effect, but the ionic solution and microcrystalline cellulose has a large mass ratio and a long dissolution time |
| 2 | 1-butyl-3-methylimidazolium chloride | 5 | 3 | 110° C. | IL is preheated to liquid state and mixed with microcrystalline cellulose by stirring | 1 min | Partially dissolved, part of the microcrystalline cellulose became lumps, the solution is brown and smells like caramel, 100 mL of water is added to allow stand for stratification | Microcrystalline cellulose has a desirable dissolution effect and a short dissolution time |
| 3 | 1-butyl-3-methylimidazolium chloride | 5 | 3 | 90° C. | IL and microcrystalline cellulose are co-heated, stirred for 20 sec every 5 min | 4 h | Partially dissolved, part of the microcrystalline cellulose became lumps | Microcrystalline cellulose has a common dissolution effect and a long dissolution time |
| 4 | 1-butyl-3-methylimidazolium borate | 10 | 1 | 90° C. | IL and microcrystalline cellulose are co-heated, stirred for 20 sec every 5 min | 40 min | Microcrystalline cellulose mixed with ionic liquid to form lumps | Microcrystalline cellulose has a poor dissolution effect |
| 5 | 1-butyl-3-methylimidazolium borate | 2 | 1.5 | 100° C. | IL is preheated to liquid state, microcrystalline cellulose is added, and stirred for 20 sec every 5 min | 4 h | Microcrystalline cellulose mixed with ionic liquid to form lumps | Microcrystalline cellulose has a poor dissolution effect |

TABLE 1-continued

| No. | Types of ionic solutions | Ionic solution/g | Microcrystalline cellulose/g | Experimental temperature | Treatment | Dissolution time | Dissolved state | Conclusion |
|---|---|---|---|---|---|---|---|---|
| 6 | 1-butyl-3-methylimidazolium borate | 2 | 1.5 | 100° C. | IL is preheated to liquid state, microcrystalline cellulose is added, and stirred for 20 sec every 5 min | 4 h | Microcrystalline cellulose mixed with ionic liquid to form lumps | Microcrystalline cellulose has a poor dissolution effect |
| 7 | 1-butyl-3-methylimidazolium borate | 10 | 6 | 90° C. | IL and microcrystalline cellulose are co-heated, stirred for 20 sec every 5 min | 4 h | Microcrystalline cellulose mixed with ionic liquid to form lumps | Microcrystalline cellulose has a poor dissolution effect |
| 8 | 1-allyl-3-methylimidazolium chloride | 10 | 1 | 90° C. | IL and microcrystalline cellulose are co-heated, stirred for 20 sec every 5 min | 40 min | Microcrystalline cellulose dissolves, but newly-added microcrystalline cellulose has increased viscosity and microcrystalline cellulose does not dissolve | Microcrystalline cellulose has a desirable dissolution effect and a long dissolution time |
| 9 | 1-allyl-3-methylimidazolium chloride | 5 | 1 | 100° C. | IL is heated to 100° C., microcrystalline cellulose is added, and stirred for 20 sec every 5 min | 20 min | Dissolved, but the solution has a high viscosity and is in a form of a hard lamella after adding water | Microcrystalline cellulose has a common dissolution effect and a long dissolution time |
| 10 | 1-allyl-3-methylimidazolium chloride | 5 | 2 | 100° C. | The microcrystalline cellulose is soaked in IL for 20 h, co-heated in a water bath, stirred for 20 sec every 5 min | 10 min | Dissolved, but the solution has an extremely viscosity, almost being solid | Microcrystalline cellulose has a common dissolution effect and a long dissolution time |
| 11 | 1-allyl-3-methylimidazolium chloride | 5 | 3 | 90° C. | IL and microcrystalline cellulose are co-heated, stirred for 20 sec every 5 min | 4 h | Microcrystalline cellulose mixed with ionic liquid to form lumps | Microcrystalline cellulose has a poor dissolution effect |
| 12 | 1-butyl-3-methylimidazole acetate | 10 | 1 | 90° C. | IL and microcrystalline cellulose are co-heated, stirred for 20 sec every 5 min | 40 min | Microcrystalline cellulose dissolves, but newly-added microcrystalline cellulose has increased viscosity and microcrystalline cellulose does not dissolve | Microcrystalline cellulose has a desirable dissolution effect and a long dissolution time |

TABLE 1-continued

| No. | Types of ionic solutions | Ionic solution/g | Microcrystalline cellulose/g | Experimental temperature | Treatment | Dissolution time | Dissolved state | Conclusion |
|---|---|---|---|---|---|---|---|---|
| 13 | 1-butyl-3-methylimidazole acetate | 10 | 6 | 90° C. | IL and microcrystalline cellulose are co-heated, stirred for 20 sec every 5 min | 4 h | Microcrystalline cellulose mixed with ionic liquid to form lumps | Microcrystalline cellulose has a poor dissolution effect |

Example 2 Screening of Addition Ratio of Ionic Liquid and Cellulose and Experimental Temperatures According to the results of Example 1, this example aimed to further screen a mixing ratio of the ionic liquid (1-butyl-3-methylimidazolium chloride) and the cellulose and suitable experimental conditions The treatment method included: 1) after microwave heating, the 1-butyl-3-methylimidazolium chloride was mixed with the cellulose in proportion, and the microwave heating was continued; 2) the 1-butyl-3-methylimidazolium chloride was mixed with the cellulose in proportion, followed by microwave heating; during the heating, the stirring treatment was conducted, a degree of dissolution was observed, and a dissolution time was recorded. The specific operation and experimental results were shown in Table 2. The cellulose in treatment 6 to 10 is fully dissolved, and the ionic solution and the microcrystalline cellulose has a mass ratio of 5:2 to 10:1; the experimental conditions are as follows: the IL is heated to 90° C., added with cellulose, stirred for 20 sec, and heated to 120° C., stirred for 20 sec, and repeatedly heated to over 120° C.; when heated to 120° C., the system turns black and has a caramel smell, and the cellulose is dissolved after repeated heating to 180° C.

TABLE 2

| No. | Ionic solution Gram | Micro-crystalline cellulose (g) | Treatment | Dissolved state | Conclusion |
|---|---|---|---|---|---|
| Treat-ment 1 | 10 | 1 | IL and microcrystalline cellulose are co-heated to 90° C., stirred for 20 sec, heated to 90° C., stirred for 20 sec, and the operations are repeated | Microcrystalline cellulose does not dissolve, and the microcrystalline cellulose is mixed with ionic liquid to forms lumps, with a poor dissolution effect | Poor dissolution effect |
| Treat-ment 2 | 10 | 1 | IL is heated to 90° C. and added with microcrystalline cellulose, stirred for 20 sec, heated to 90° C., stirred for 20 sec, and operations are repeated | After repeated heating several times, a small part of microcrystalline cellulose is dissolved in the ionic liquid, and most of fibers are mixed with part of the ionic liquid to form lumps | Common dissolution effect |
| Treat-ment 3 | 10 | 1 | IL is heated to 90° C. and added with microcrystalline cellulose, stirred for 20 sec, heated to 100° C., stirred for 20 sec, and heating to 100° C. is repeated | After repeated heating several times, part of microcrystalline cellulose is dissolved, and part of fibers are mixed with part of the ionic liquid to form lumps | Common dissolution effect |
| Treat-ment 4 | 10 | 1 | IL is heated to 90° C. and added with microcrystalline cellulose, stirred for 20 sec, heated to 110° C., stirred for 20 sec, and heating to 110° C. is repeated | After repeated heating several times, the system turns yellow, part of microcrystalline cellulose is dissolved, and part of fibers are mixed with part of the ionic liquid to form lumps | Common dissolution effect |
| Treat-ment 5 | 10 | 1 | IL is heated to 90° C. and added with microcrystalline cellulose, stirred for 20 sec, heated to 120° C., stirred for 20 sec, and heating to 120° C. is repeated | When heated to 120° C., the system turns black and has a caramel smell; after repeated heating several times, the microcrystalline cellulose is partially dissolved, and part of fibers are mixed with part of ionic liquid to form bumps | Common dissolution effect |

TABLE 2-continued

| No. | Ionic solution Gram | Micro-crystalline cellulose (g) | Treatment | Dissolved state | Conclusion |
|---|---|---|---|---|---|
| Treatment 6 | 10 | 1 | IL is heated to 90° C. and added with microcrystalline cellulose, stirred for 20 sec, heated to 120° C., stirred for 20 sec, and heating to 180° C. is repeated | When heated to 120° C., the system turns black and has a caramel smell; after repeated heating to 180° C., the microcrystalline cellulose dissolves | Desirable dissolution effect |
| Treatment 7 | 8 | 1 | IL is heated to 90° C. and added with microcrystalline cellulose, stirred for 20 sec, heated to 120° C., stirred for 20 sec, and heating to 180° C. is repeated | When heated to 120° C., the system turns black and has a caramel smell; after repeated heating to 180° C., the microcrystalline cellulose dissolves | Desirable dissolution effect |
| Treatment 8 | 5 | 1 | IL is heated to 90° C. and added with microcrystalline cellulose, stirred for 20 sec, heated to 180° C., stirred for 20 sec, and heating to 180° C. is repeated | When heated to 120° C., the system turns black and has a caramel smell; after repeated heating to 180° C., the microcrystalline cellulose dissolves | Desirable dissolution effect |
| Treatment 9 | 5 | 1.5 | IL is heated to 90° C. and added with microcrystalline cellulose, stirred for 20 sec, heated to 120° C., stirred for 20 sec, and heating to 180° C. is repeated | When heated to 120° C., the system turns black and has a caramel smell; after repeated heating to 180° C., the microcrystalline cellulose dissolves | Desirable dissolution effect |
| Treatment 10 | 5 | 2 | IL is heated to 90° C. and added with microcrystalline cellulose, stirred for 20 sec, heated to 120° C., stirred for 20 sec, and heating to 180° C. is repeated | When heated to 120° C., the system turns black and has a caramel smell; after repeated heating to 180° C., the microcrystalline cellulose dissolves | Desirable dissolution effect |
| Treatment 11 | 5 | 2.5 | IL is heated to 90° C. and added with microcrystalline cellulose, stirred for 20 sec, heated to 120° C., stirred for 20 sec, and heating to 180° C. is repeated | When heated to 120° C., the system turns black and has a caramel smell; after repeated heating to 120° C., the microcrystalline cellulose is mostly dissolved, and flaky insolubles are formed | Desirable dissolution effect, an added amount of microcrystal line cellulose has exceeded a maximum dissolving amount of cellulose under this condition |

Example 3 Screening of Ionic Solution Concentrations in Microbial Medium

Due to the toxicity of ionic liquid, if the carbon source contains a large amount of ionic liquid, the prepared medium is not conducive to the growth of strains. Therefore, a purpose of this example is to screen a concentration range of the ionic liquid contained in the medium. In an LB solid medium (including yeast powder: 10 g/L, peptone: 5 g/L, NaCl: 10 g/L, and agar: 18 g/L), different proportions of ionic liquid (1-butyl-3-methylimidazolium chloride) were added, followed by coating with *Escherichia coli*, and a growth state for 48 h was observed. The specific results are shown in Table 3. The *Escherichia coli* grows normally when the ionic solution concentration is 2%; and the growth of *Escherichia coli* is inhibited when the ionic liquid concentration reaches not less than 3%. Therefore, the concentration of the ionic liquid in the medium during microbial culture should not exceed 3%.

TABLE 3

| Ionic solution concentration | Growth state of strains |
|---|---|
| 0% | Normal |
| 1% | Normal |
| 2% | Normal |
| 3% | Slightly inhibited growth |
| 4% | Inhibited growth |
| 5% | Inhibited growth |
| 6% | No growth |
| 7% | No growth |

Example 4 Verification of Strain Culture Ability of Novel Microbial Medium with Ionic Liquid-Pretreated Cellulose as Carbon Source In this example, a carbon source obtained by optimizing experimental conditions is applied; functional verification is conducted on a medium containing a liquid cellulose-based carbon source and a medium prepared from a fractionated product obtained after recovery of ionic liquid; and an ability of a novel medium is determined to culture multiple strains of different species.

Experiment 1

1) Licorice straw was pulverized using a Chinese herbal medicine grinder, and sieved through a 30-mesh sieve to obtain a licorice straw powder. Ionic liquid (1-butyl-3-methylimidazolium chloride) was mixed with the licorice straw powder in a mass ratio of 5:2, the ionic liquid was added to a beaker and heated to 90° C., and the ionic liquid was completely melted into transparent, colorless and viscous liquid. The licorice straw powder was added to the completely melted ionic liquid, stirred with a glass rod, and heated to 120° C.; when a mixture of the licorice straw powder and the ionic liquid began to turn black, heating was terminated, followed by stirring for 20 sec. The mixture was heated to 180° C., followed by stopping heating, and stirring for 20 sec (repeating 3 times). 2 times volume of distilled water was added to a beaker, and stirred with the glass rod, the mixture was dissolved and filtered with a rapid qualitative filter paper. Distilled water was added to a filtrate to control a concentration of the ionic liquid in the carbon source, to further control a concentration of the ionic liquid in the new medium. A mass of the ionic liquid and a dilution volume had a ratio of 1 g:50 mL.

In the solution after dilution, $NH_4Cl$ (2 g/L), $MgSO_4$ (0.2 g/L), and NaCl (10 g/L) were added in proportion, followed by conducting autoclaving at 115° C. for 15 min. *Brevibacterium casei, Bacillus, Micrococcus luteus* and *Escherichia coli* with a 3% inoculum ($OD_{600}$=0.5 to 0.6) were inoculated into the mixture above. Shaker culture was conducted at 37° C., 150 rpm. From a growth curve (FIG. 1), it can be seen that the *Brevibacterium casei* and *Bacillus* in this medium have a relatively high proliferation rate and a desirable growth state, indicating that the medium obtained by this method has a desirable culture effect.

Experiment 2

1) The ionic liquid and the microcrystalline cellulose were mixed in a mass ratio of 5:2. The ionic liquid was added to the beaker and heated to 90° C., and the ionic liquid was completely melted into transparent, colorless and viscous liquid. The microcrystalline cellulose was added to the completely melted ionic liquid, and stirred with the glass rod for 20 sec. Heating was continued to 120° C., a mixture of the microcrystalline cellulose and the ionic liquid began to turn black, and heating was terminated, followed by stirring with the glass rod for 20 sec. The mixture was heated to 180° C., followed by stopping heating, and stirring for 20 sec (repeating 3 times). 2 times volume of distilled water was added to a beaker, and stirred with the glass rod, the mixture was dissolved and filtered with a rapid qualitative filter paper. The distilled water was added to dilute a filtrate, where a mass of dissolved microcrystalline cellulose and a dilution volume had a ratio of 1 g:40 mL.

2) A solution obtained in the previous step was fractionated using a rotary evaporator at a pressure of −0.080 Mpa, at 25° C. and then 80° C. in a water bath, respectively (a boiling point changed once), and a rotation speed of 50 rpm; after the fractionation, colorless and transparent liquid was obtained in a collection bottle, and ionic liquid was obtained in an evaporation bottle.

Figure 2:
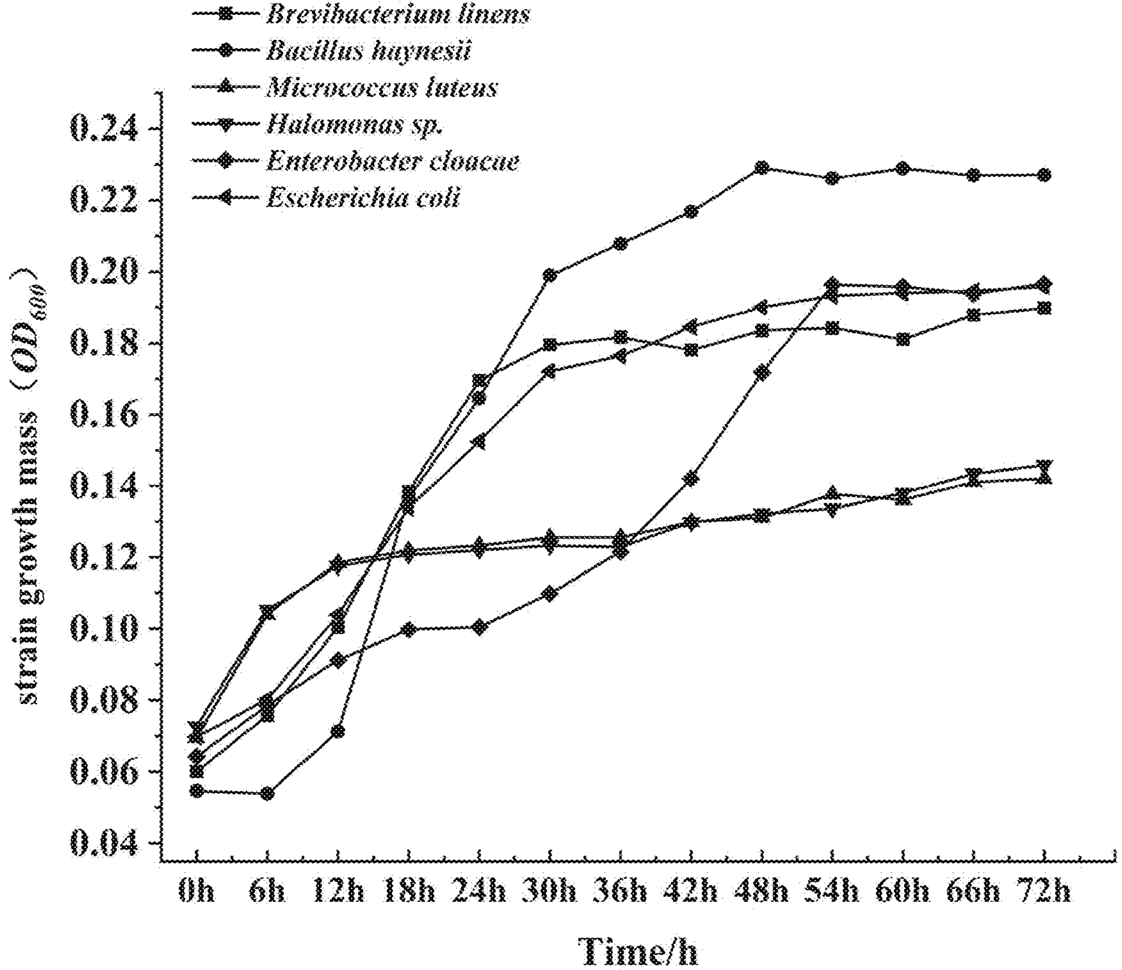
FIG. 2 shows a growth curve diagram of *Brevibacterium casei, Bacillus, Micrococcus luteus*, and *Escherichia coli* in a medium with liquefied licorice straw as a carbon source in an example of the present disclosure.

(3) In a recovery bottle solution (a carbon source without ionic liquid), $NH_4Cl$ (2 g/L), $MgSO_4$ (0.2 g/L), and NaCl (10 g/L) were added in proportion, followed by conducting autoclaving at 115° C. for 15 min. *Brevibacterium casei, Bacillus, Micrococcus luteus, Enterobacter cloacae, Halomonas*, and *Escherichia coli* with a 3% inoculum ($OD_{600}$=0.5 to 0.6) were inoculated into the mixture above. Shaker culture was conducted at 37° C., 150 rpm. From a growth curve (FIG. 2), it can be seen that the *Brevibacterium casei, Bacillus, Micrococcus luteus, Enterobacter cloacae, Halomonas*, and *Escherichia coli* can proliferate in this medium, indicating that the medium obtained by this method has certain microbial culture ability.

Experiment 3

The ionic liquid recovered in Experiment 2 of the example was mixed with microcrystalline cellulose in a mass ratio of 5:2. The ionic liquid was added to the beaker, heated to 130° C., microcrystalline cellulose was added to the ionic liquid, and stirred with a glass rod for 20 sec. The mixture was heated to 180° C., followed by stirring for 20 sec (repeating 3 times). 2 times volume of distilled water was added to a beaker, and stirred with the glass rod, the mixture was dissolved and filtered with a rapid qualitative filter paper. The distilled water was added to dilute a filtrate, where a mass of dissolved microcrystalline cellulose and a dilution volume had a ratio of 1 g:40 mL.

2) A solution obtained in the previous step was fractionated using a rotary evaporator at a pressure of −0.075 Mpa, at 35° C. and then 75° C. in a water bath, respectively (a boiling point changed once), and a rotation speed of 50 rpm; after the fractionation, colorless and transparent liquid was obtained in a collection bottle, and ionic liquid was obtained in an evaporation bottle.

(3) in the solution in the recovery bottle, $NH_4Cl$ (2 g/L), $MgSO_4$ (0.2 g/L), and NaCl (10 g/L) are added in proportion, followed by conducting autoclaving at 115° C. for 15 min. *Brevibacterium casei* and *Escherichia coli* with a 3% inoculum ($OD_{600}$=0.5 to 0.6) were inoculated into the mixture above. Shaker culture was conducted at 37° C., 150 rpm. The changes of $OD_{600}$ with time are shown in Table 4. From the $OD_{600}$, it can be seen that the *Brevibacterium casei* and *Escherichia coli* can proliferate in this medium, indicating that the medium obtained by this method has certain microbial culture ability.

TABLE 4

| Item | $OD_{600}$ 0 h | $OD_{600}$ 24 h | $OD_{600}$ 48 h | $OD_{600}$ 72 h |
|---|---|---|---|---|
| *Escherichia coli* | 0.0730 | 0.1465 | 0.1978 | 0.1998 |
| *Brevibacterium casei* | 0.0632 | 0.1525 | 0.1834 | 0.1820 |

Experiment 4

The ionic liquid recovered in Experiment 3 of the example was mixed with microcrystalline cellulose in a mass ratio of 5:2. The ionic liquid was added to the beaker, heated to 130° C., microcrystalline cellulose was added to the ionic liquid, and stirred with a glass rod for 20 sec; heating was continued to 180° C., stirred with the glass rod for 20 sec, repeating 3 times. 2 times volume of distilled water was added to a beaker, and stirred with the glass rod, the mixture was dissolved and filtered with a rapid qualitative filter paper. The distilled water was added to dilute a filtrate, where a mass of dissolved microcrystalline cellulose and a dilution volume had a ratio of 1 g:40 mL.

2) A solution obtained in the previous step was fractionated using a rotary evaporator at a pressure of −0.075 Mpa, at 35° C. and then 75° C. in a water bath, respectively (a boiling point changed once), and a rotation speed of 50 rpm; after the fractionation, colorless and transparent liquid was obtained in a collection bottle, and ionic liquid was obtained in an evaporation bottle.

(3) in the solution in the recovery bottle, $NH_4Cl$ (2 g/L), $MgSO_4$ (0.2 g/L), and NaCl (10 g/L) are added in proportion, followed by conducting autoclaving at 115° C. for 15 min. *Brevibacterium casei* and *Escherichia coli* with a 3% inoculum ($OD_{600}$=0.5 to 0.6) were inoculated into the mixture above. Shaker culture was conducted at 37° C., 150 rpm. The changes of $OD_{600}$ with time are shown in Table 5. From the $OD_{600}$, it can be seen that the *Brevibacterium casei* and *Escherichia coli* can proliferate in this medium, indicating that the medium obtained by this method has certain microbial culture ability.

TABLE 5

| Item | $OD_{600}$ 0 h | $OD_{600}$ 24 h | $OD_{600}$ 48 h | $OD_{600}$ 72 h |
|---|---|---|---|---|
| *Escherichia coli* | 0.0716 | 0.1321 | 0.1821 | 0.1878 |
| *Brevibacterium casei* | 0.0655 | 0.1644 | 0.1964 | 0.1920 |

Example 5 Screening of Experimental Temperatures of NaOH/Urea and Cellulose

In this example, experimental conditions for treating cellulose with a NaOH/Urea solution system were screened. The specific experimental conditions, operations and experimental results were as follows:

1) A solution of 4% NaOH/7% Urea was prepared, and 1 g/L microcrystalline cellulose was added to the solution; a resulting NaOH/Urea-microcrystalline cellulose solution was turbid at room temperature, and the microcrystalline cellulose precipitated to a bottom of the solution after standing. This indicates that microcrystalline cellulose is insoluble in this solution system at room temperature.

2) A solution of 4% NaOH/7% Urea was prepared, 14 g/L microcrystalline cellulose was added to the solution, frozen at −10° C. for 24 h, and thawed at room temperature; when being heated to −14° C., the solution was in a state of an ice-water mixture. The stirring was conducted, and a NaOH/Urea-microcrystalline cellulose solution was gradually clarified, indicating that the cellulose was completely dissolved. Therefore, this experimental condition could be used to pretreat microcrystalline cellulose.

3) A solution of 4% NaOH/7% Urea was prepared, 15 g/L microcrystalline cellulose was added to the solution, frozen at −20° C. for 24 h, and thawed at room temperature; when being heated to −14° C., the solution was in a state of an ice-water mixture. The stirring was conducted, and flakes of cellulose were precipitated at the bottom of the NaOH/Urea-cellulose solution, indicating that the solution system had reached the highest cellulose dissolving capacity.

Example 6 Screening of Concentrations of NaOH and Urea

In this example, concentrations of NaOH and Urea were screened. The specific experimental conditions, operations and experimental results were as follows:

1) A 3% NaOH solution was prepared, Urea at concentrations of 7, 8, 10, 12, and 14(%) were added to the solution, respectively, 5 g of microcrystalline cellulose was added to the NaOH/Urea solution systems of different concentrations, frozen at −20° C., and thawed at room temperature; when being heated to −14° C., the solution was in a state of an ice-water mixture. The stirring was conducted, and the microcrystalline cellulose was insoluble.

Figure 3:
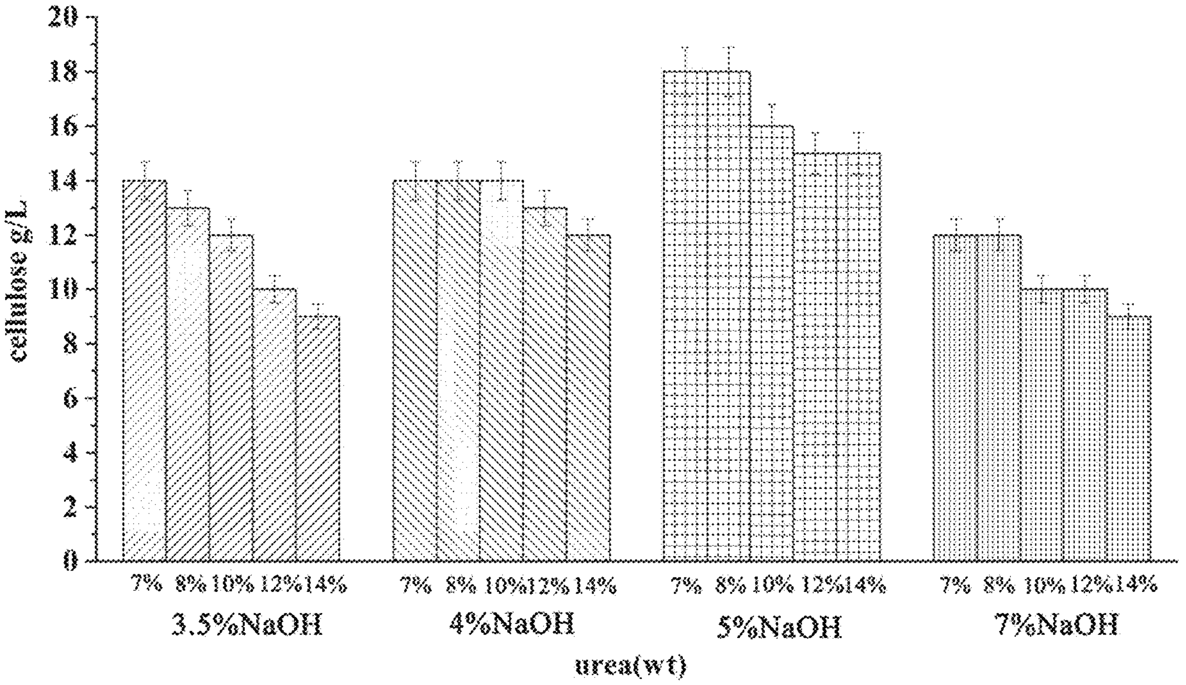
FIG. 3 shows a result of a maximum dissolving amount of cellulose in a liquefaction experiment of the cellulose by a NaOH/Urea solution in an example of the present disclosure.

2) A 3.5% NaOH solution was prepared, Urea at of 7, 8, 10, 12, and 14(%) were added to the solution, respectively, microcrystalline cellulose was added to the NaOH/Urea solution systems of different concentrations, frozen at −20° C., and thawed at room temperature; when being heated to −14° C., the solution was in a state of an ice-water mixture. The stirring was conducted, and dissolved amounts of the microcrystalline cellulose were 10 g/L, 10 g/L, 9 g/L, 9 g/L, and 8 g/L in sequence. The results are shown in FIG. 3.

3) A 4% NaOH solution was prepared, Urea at of 7, 8, 10, 12, and 14(%) were added to the solution, respectively, microcrystalline cellulose was added to the NaOH/Urea solution systems of different concentrations, frozen at −20° C., and thawed at room temperature; when being heated to −14° C., the solution was in a state of an ice-water mixture. The stirring was conducted, and dissolved amounts of the microcrystalline cellulose were 14 g/L, 14 g/L, 14 g/L, 13 g/L, and 12 g/L in sequence. The results are shown in FIG. 3.

4) A 5% NaOH solution was prepared, Urea at of 7, 8, 10, 12, and 14(%) were added to the solution, respectively, microcrystalline cellulose was added to the NaOH/Urea solution systems of different concentrations, frozen at −20° C., and thawed at room temperature; when being heated to −14° C., the solution was in a state of an ice-water mixture. The stirring was conducted, and dissolved amounts of the microcrystalline cellulose were 18 g/L, 18 g/L, 16 g/L, 15 g/L, and 15 g/L in sequence. The results are shown in FIG. 3.

5) A 7% NaOH solution was prepared, Urea at of 7, 8, 10, 12, and 14(%) were added to the solution, respectively, microcrystalline cellulose was added to the NaOH/Urea solution systems of different concentrations, frozen at −20° C., and thawed at room temperature; when being heated to −14° C., the solution was in a state of an ice-water mixture. The stirring was conducted, and dissolved amounts of the microcrystalline cellulose were 12 g/L, 12 g/L, 10 g/L, 10 g/L, and 9 g/L in sequence. The results are shown in FIG. 3.

Figure 4:
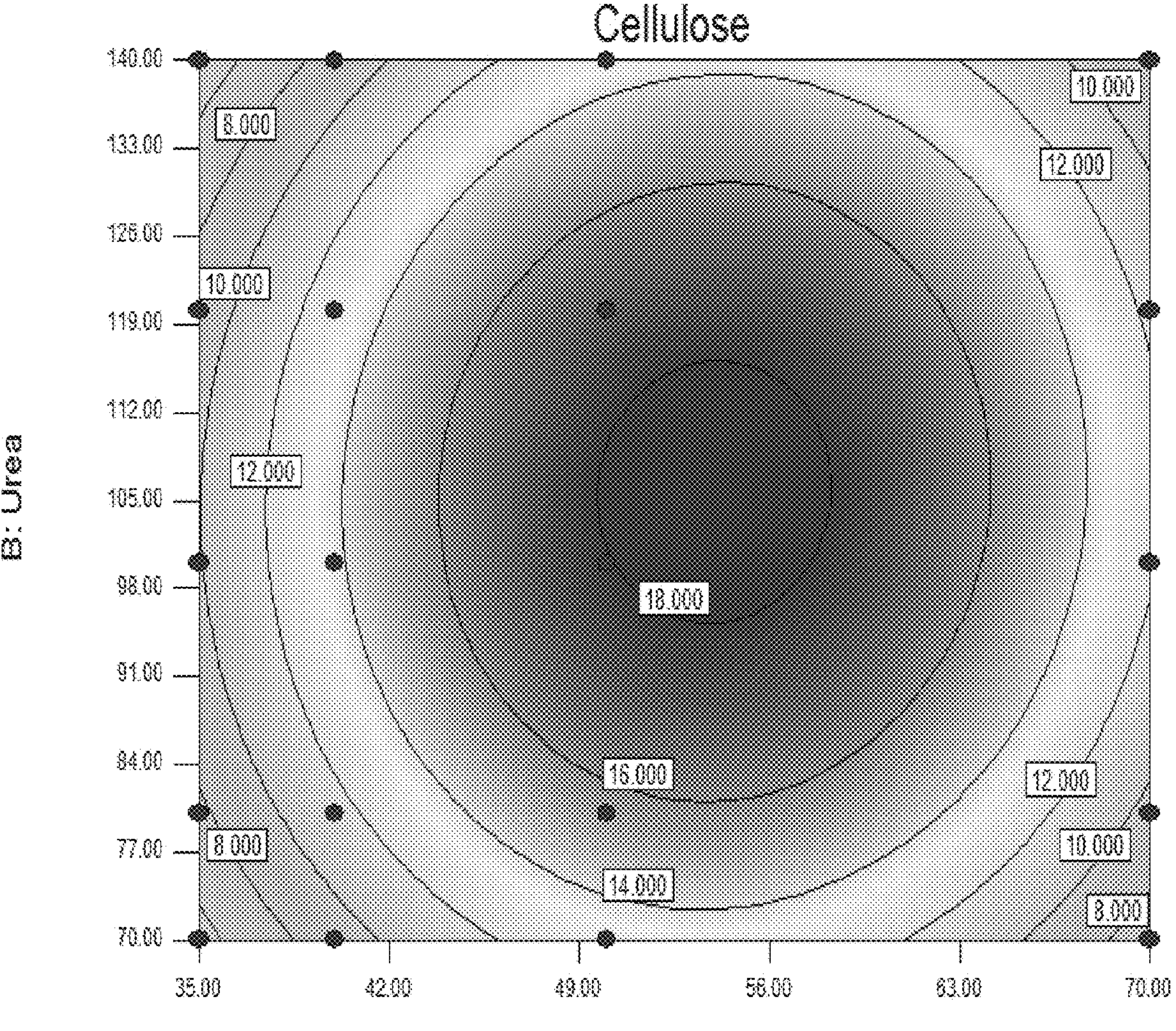
FIG. 4 shows a two-dimensional contour map of measured and predicted values of the cellulose drawn by a dissolved amount of microcrystalline cellulose as a response value in an example of the present disclosure.
Figure 5:
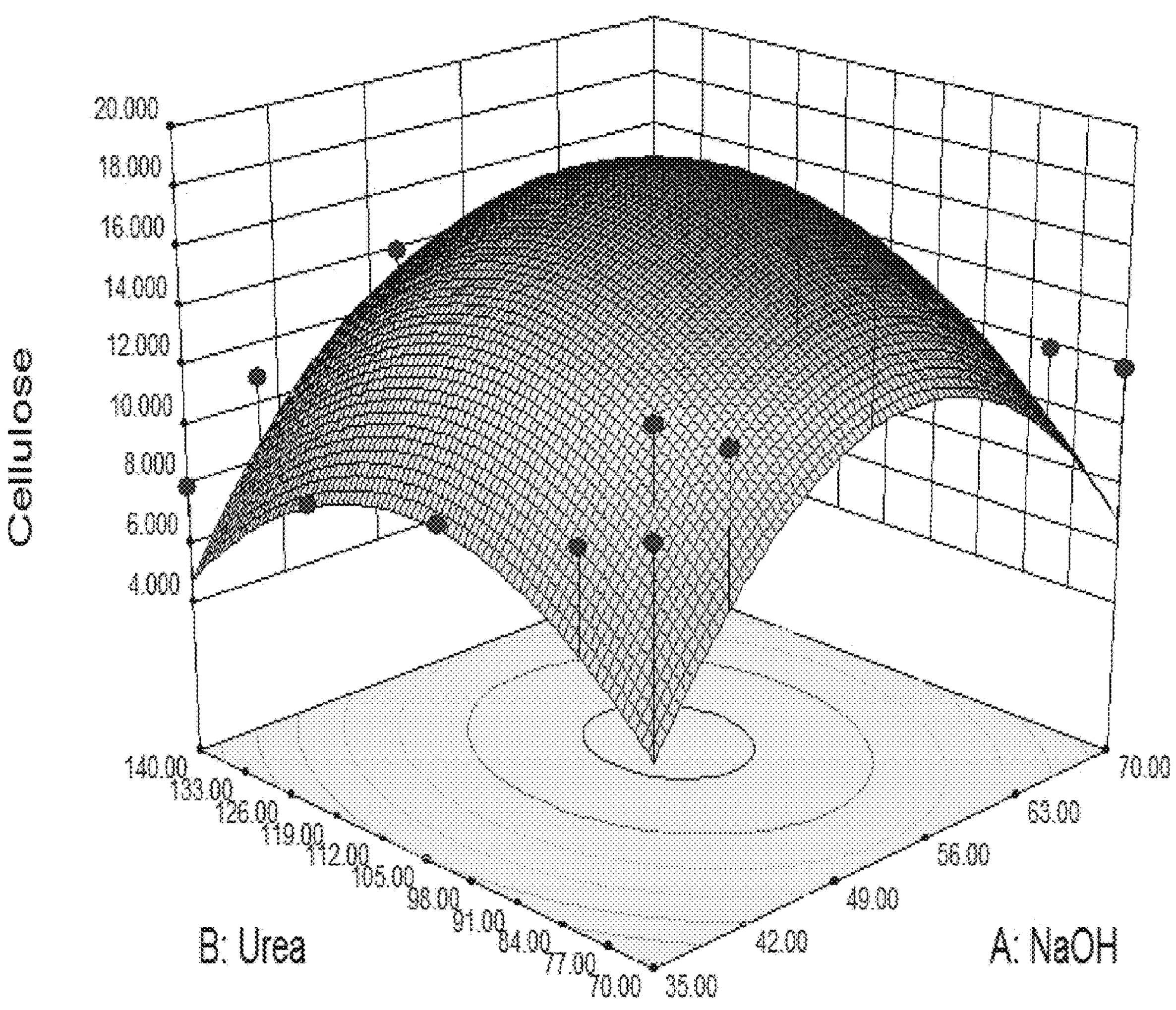
FIG. 5 shows a three-dimensional response surface graph of measured and predicted values of the cellulose drawn by a dissolved amount of microcrystalline cellulose as a response value in an example of the present disclosure.

6) By using a dissolved amount of microcrystalline cellulose as a response value, a response analysis table was constructed for a test value and a predicted value of the cellulose, as shown in Table 6. A two-dimensional contour map and a three-dimensional response surface map were drawn, respectively (as shown in FIG. 4 and FIG. 5). The analysis of the response of cellulose solutions of each ratio shows that, an optimal ratio is 4% NaOH/7% Urea (as shown in Table 7), and the microcrystalline cellulose has a maximum dissolved amount of 14 g/L.

TABLE 6

| r standard order | Actual value | Predicted Value | Residual | Influence | Studentized internal residual error | Studentized external residual error | Fit value effect | Cook's distance | Running sequence |
|---|---|---|---|---|---|---|---|---|---|
| 1 | 14 | 9.04 | 4.96 | 0.09 | 1.29 | 1.31 | 0.40 | 0.03 | 8 |
| 2 | 0 | 9.79 | −9.79 | 0.22 | −2.76 | −3.27 | −1.73 | 0.35 | 13 |
| 3 | 8 | 4.77 | 3.23 | 0.24 | 0.92 | 0.92 | 0.51 | 0.04 | 6 |
| 4 | 9 | 8.94 | 0.06 | 0.10 | 0.02 | 0.02 | 0.01 | 0.00 | 5 |
| 5 | 0 | 5.86 | −5.86 | 0.17 | −1.60 | −1.65 | −0.74 | 0.08 | 7 |
| 6 | 18 | 15.48 | 2.52 | 0.13 | 0.67 | 0.67 | 0.26 | 0.01 | 15 |
| 7 | 16 | 17.95 | −1.95 | 0.17 | −0.53 | −0.52 | −0.24 | 0.01 | 16 |
| 8 | 12 | 5.26 | 6.74 | 0.09 | 1.76 | 1.84 | 0.58 | 0.05 | 2 |
| 9 | 18 | 13.04 | 4.96 | 0.14 | 1.33 | 1.35 | 0.54 | 0.05 | 14 |
| 10 | 11 | 8.78 | 2.22 | 0.21 | 0.62 | 0.61 | 0.32 | 0.02 | 12 |
| 11 | 0 | 2.12 | −2.12 | 0.18 | −0.58 | −0.57 | −0.27 | 0.01 | 1 |
| 12 | 13 | 13.75 | −0.75 | 0.12 | −0.20 | −0.20 | −0.07 | 0.00 | 10 |
| 13 | 10 | 9.88 | 0.12 | 0.11 | 0.03 | 0.03 | 0.01 | 0.00 | 4 |
| 14 | 11 | 7.61 | 3.39 | 0.08 | 0.88 | 0.88 | 0.26 | 0.01 | 3 |
| 15 | 14 | 11.41 | 2.59 | 0.08 | 0.67 | 0.66 | 0.20 | 0.01 | 9 |
| 16 | 14 | 17.20 | −3.20 | 0.15 | −0.87 | −0.86 | −0.37 | 0.02 | 17 |
| 17 | 14 | 13.24 | 0.76 | 0.26 | 0.22 | 0.22 | 0.13 | 0.00 | 18 |
| 18 | 12 | 12.87 | −0.87 | 0.10 | −0.23 | −0.22 | −0.07 | 0.00 | 11 |
| 19 | 0 | 3.49 | −3.49 | 0.43 # | −1.15 | −1.16 | −1.01 | 0.17 | 19 |
| 20 | 12 | 6.87 | 5.13 | 0.27 | 1.50 | 1.54 | 0.95 | 0.14 | 20 |
| 21 | 12 | 9.44 | 2.56 | 0.22 | 0.72 | 0.71 | 0.38 | 0.02 | 21 |
| 22 | 11 | 12.17 | −1.17 | 0.23 | −0.33 | −0.33 | −0.18 | 0.01 | 22 |
| 23 | 10 | 11.69 | −1.69 | 0.29 | −0.50 | −0.49 | −0.31 | 0.02 | 23 |
| 24 | 8 | 7.99 | 0.01 | 0.57 # | 0.01 | 0.01 | 0.01 | 0.00 | 24 |
| 25 | 0 | −2.81 | 2.81 | 0.28 | 0.82 | 0.82 | 0.51 | 0.04 | 25 |
| 26 | 0 | 0.31 | −0.31 | 0.18 | −0.08 | −0.08 | −0.04 | 0.00 | 26 |
| 27 | 0 | 2.62 | −2.62 | 0.16 | −0.71 | −0.70 | −0.30 | 0.02 | 27 |
| 28 | 0 | 4.83 | −4.83 | 0.18 | −1.33 | −1.35 | −0.64 | 0.07 | 28 |
| 29 | 0 | 3.82 | −3.82 | 0.19 | −1.06 | −1.06 | −0.51 | 0.04 | 29 |
| 30 | 0 | −0.41 | 0.41 | 0.36 | 0.13 | 0.13 | 0.09 | 0.00 | 30 |

TABLE 7

| No. | NaOH (g/L) | Urea (g/L) | Microcrystalline cellulose (g/L) | No. | NaOH (g/L) | Urea (g/L) | Microcrystalline cellulose (g/L) |
|---|---|---|---|---|---|---|---|
| 8 | 40 | 70 | 14 | 17 | 50 | 120 | 14 |
| 13 | 50 | 60 | 0 | 18 | 50 | 140 | 14 |
| 6 | 35 | 140 | 8 | 11 | 40 | 120 | 12 |
| 5 | 35 | 120 | 9 | 19 | 70 | 60 | 0 |
| 7 | 40 | 60 | 0 | 20 | 70 | 70 | 12 |
| 15 | 50 | 80 | 18 | 21 | 70 | 80 | 12 |
| 16 | 50 | 100 | 16 | 22 | 70 | 100 | 11 |
| 2 | 35 | 70 | 12 | 23 | 70 | 120 | 10 |
| 14 | 50 | 70 | 18 | 24 | 70 | 140 | 8 |
| 12 | 40 | 140 | 11 | 25 | 30 | 60 | 0 |
| 1 | 35 | 60 | 0 | 26 | 30 | 70 | 0 |
| 10 | 40 | 100 | 13 | 27 | 30 | 80 | 0 |
| 4 | 35 | 100 | 10 | 28 | 30 | 100 | 0 |
| 3 | 35 | 80 | 11 | 29 | 30 | 120 | 0 |
| 9 | 40 | 80 | 14 | 30 | 30 | 140 | 0 |

Example 7 Screening of pH of NaOH/Urea Solution System-Pretreated Cellulose System In this example, the experiment was continued on the basis of Example 6. By observing the pretreatment of cellulose with the NaOH/Urea solution system at different pH values, and the treatment of microcrystalline cellulose with the NaOH/Urea solution system, changes of cellulose in this solution system due to different experimental operations were observed. The specific experimental conditions, operations and experimental results were as follows:

1) A solution of 5% NaOH/10% Urea was prepared, 14 g/L microcrystalline cellulose was added to the solution, frozen at −20° C. for 24 h, and thawed at room temperature; when being heated to −14° C., the solution was in a state of an ice-water mixture. The stirring was conducted, and the solution was gradually clear (pH >14), 1 mL of the solution was used as a spare sample. The pH was adjusted to 10 with HCl, the solution turned turbid, and 1 mL of the solution was used as a spare sample. The solution was filtered through gauze and 1 mL of a filtrate was used as a spare sample.

Figure 6:
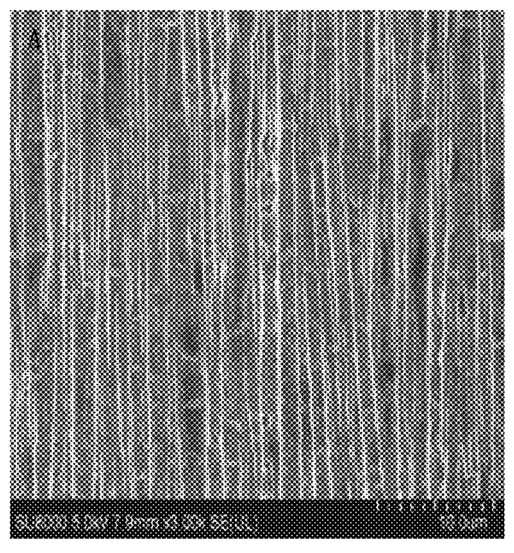
FIG. 6 shows a structural change of the cellulose in an alkaline solution after NaOH/Urea system treatment of microcrystalline cellulose in an example of the present disclosure.
Figure 6:
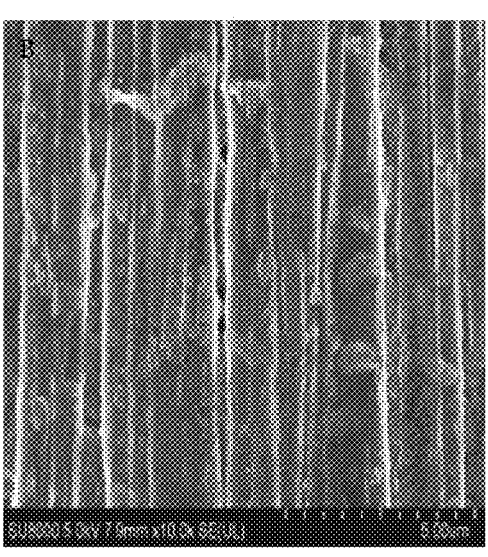
Figure 7:
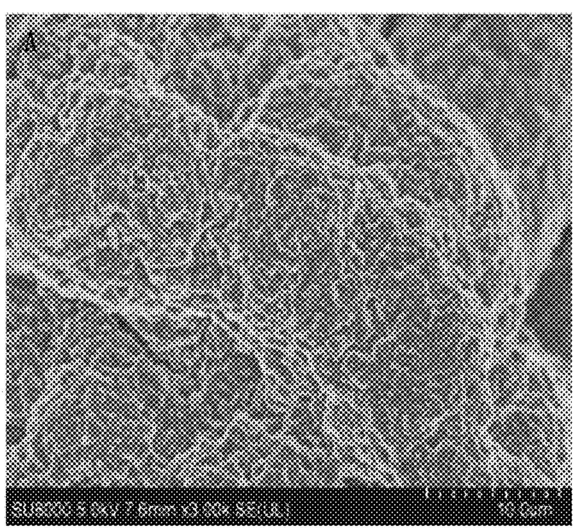
FIG. 7 shows a structural change of a filter residue precipitated by adding HCl after NaOH/Urea system treatment of microcrystalline cellulose in an example of the present disclosure.
Figure 7:
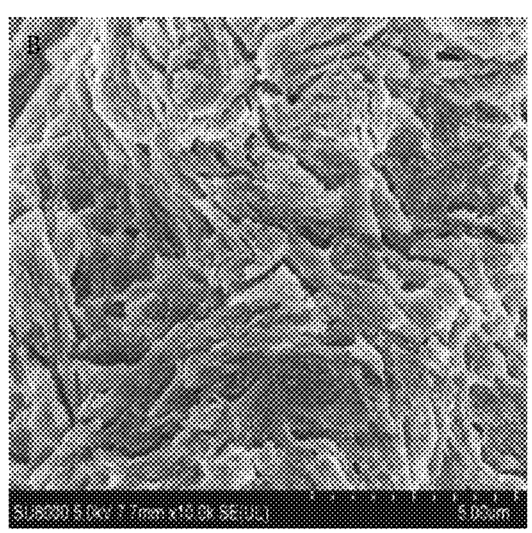
Figure 8:
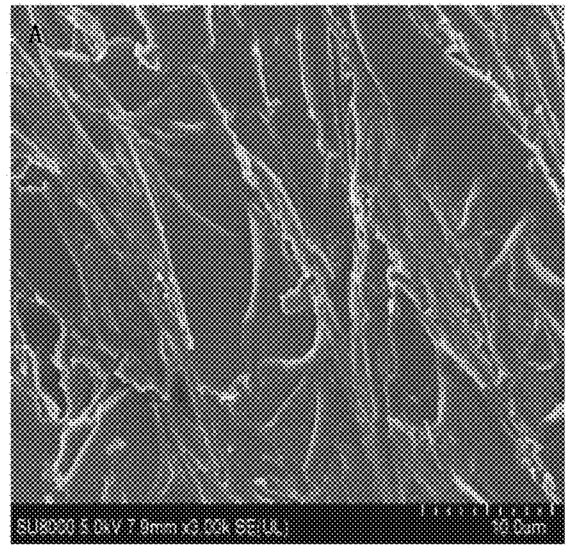
FIG. 8 shows a structural change of the cellulose in a filtrate precipitated by adding HCl after NaOH/Urea system treatment of microcrystalline cellulose in an example of the present disclosure.
Figure 8:
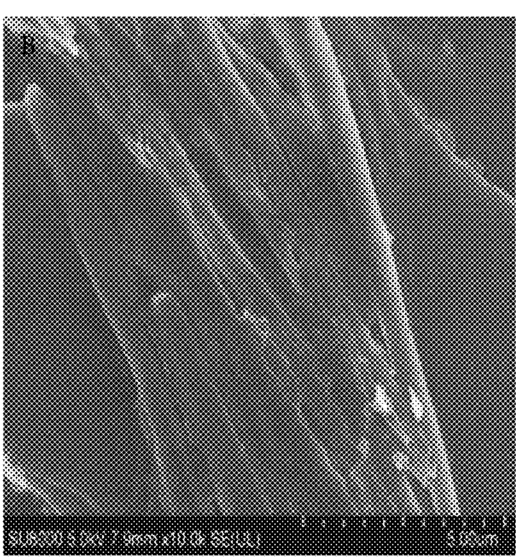

2) 1 μL of each of the three spare samples was applied to a glass slide, the slide glass was fixed with a liquid conductive adhesive on a pie-shaped battery, followed by spraying gold, and the battery was placed on a scanning electron microscope stage to collect images after spraying gold. FIG. 6 shows the NaOH/Urea-cellulose solution without HCl (pH >14), with high cellulose content and elongated shape. FIG. 7 shows the filter residues precipitated after the NaOH/Urea-cellulose solution is adjusted with the HCl, which may be the precipitated flocculent cellulose; the combination of cellulose and chloride ions breaks the intermolecular and intramolecular hydrogen bonds, making the cellulose lamellar. FIG. 8 shows the filtrate after the NaOH/Urea-cellulose solution is adjusted by adding the HCl, where the cellulose content is less than that in FIG. 6, and the shape is similar to that in FIG. 6; this indicates that during adding the HCl to adjust the pH value, although cellulose is precipitated, the filtrate still contains part of cellulose.

Example 8 Novel Medium Obtained from NaOH/Urea Solution System-Pretreated Cellulose In this example, functional verification of a NaOH/Urea-cellulose-based medium was conducted to determine an ability of the novel medium to culture multiple strains of different species.

Experiment 1

1) A solution of 4% NaOH/7% Urea was prepared, 14 g/L microcrystalline cellulose was added to the solution, frozen at −20° C. for 24 h, and thawed at room temperature; when being heated to −14° C., the solution was in a state of an ice-water mixture. The stirring was conducted, and the solution was gradually clarified. After adjusting the pH value to 10 with HCl, the solution was filtered with gauze to collect a filtrate.

2) in the filtrate, $NH_4Cl$ (2 g/L), $MgSO_4$ (0.2 g/L), and NaCl (10 g/L) were added in proportion, followed by conducting autoclaving at 115° C. for 15 min. The filtrate was inoculated with *Halomonas, Bacillus, Micrococcus luteus, Brevibacterium casei, Bacillus licheniformis* ($OD_{600}$=0.5 to 0.6), followed by conducting shake culture at 37° C., 150 rpm; all strains grew normally. After 72 h, a culture was transferred to a 50 mL centrifuge tube, centrifuged at 12,000 rpm for 10 min, and a supernatant was discarded; a resulting precipitate was pre-frozen at −70° C. for 4 h, and then lyophilized overnight in a −60° C. vacuum lyophilizer. A dry weight was weighed using a ten-thousandth balance, and dry cell weights (CDWs) were 0.381 g/L, 0.403 g/L, 0.522 g/L, 0.343 g/L, and 0.362 g/L, respectively. The *Halomonas, Bacillus, Micrococcus luteus, Brevibacterium casei* and *Bacillus licheniformis* can proliferate in this medium, indicating that the medium obtained by this method has certain microbial culture ability.

Experiment 2

1) A solution of 4% NaOH/7% Urea was prepared, 14 g/L microcrystalline cellulose was added to the solution, frozen at −20° C. for 24 h, and thawed at room temperature; when being heated to −14° C., the solution was in a state of an ice-water mixture. The stirring was conducted, and the solution was gradually clarified. After adjusting the pH value to 10 with HCl, the solution was filtered with gauze to collect a filtrate.

Figure 9:
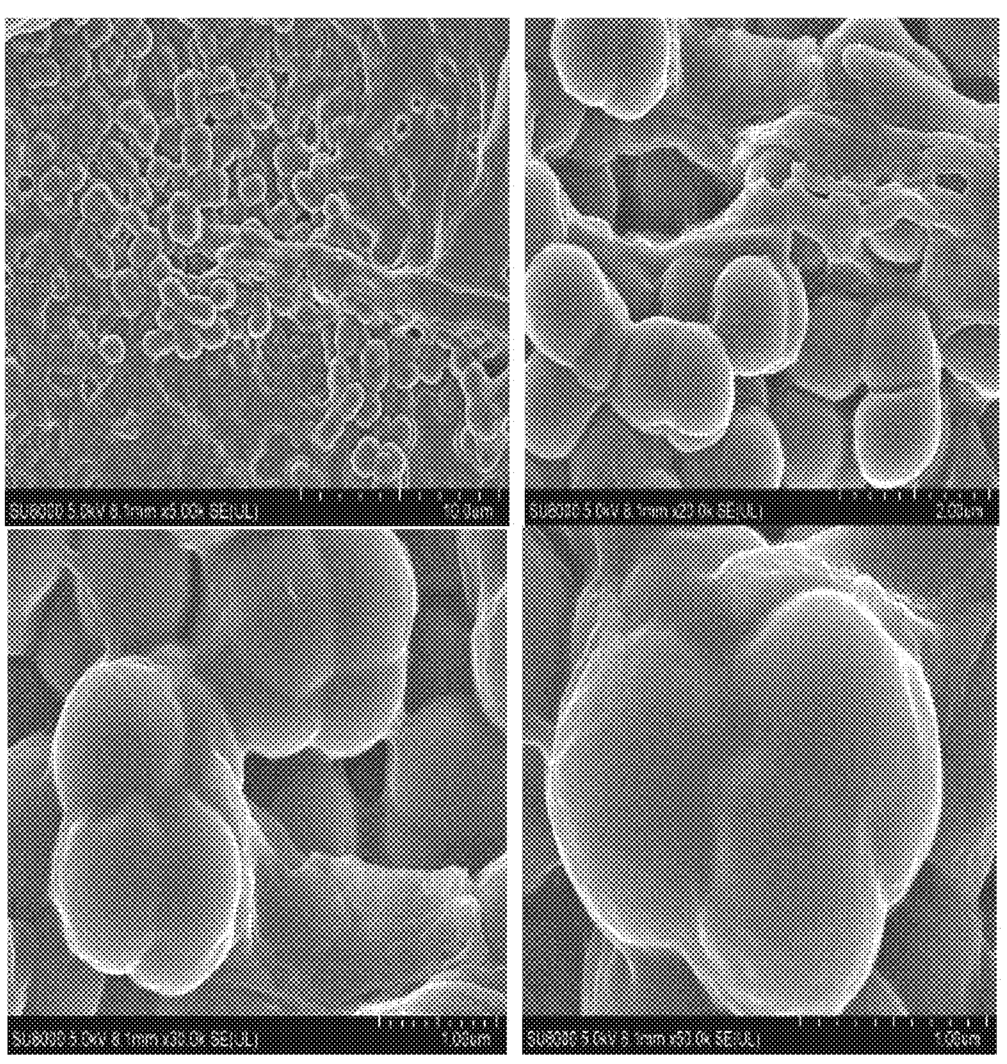
FIG. 9 shows a strain morphology of *Micrococcus luteus* after 72 h of culture with cellulose liquid obtained after NaOH/Urea system treatment of microcrystalline cellulose as a carbon source in an example of the present disclosure.

2) in the filtrate, $NH_4Cl$ (2 g/L), $MgSO_4$ (0.2 g/L), and NaCl (10 g/L) were added in proportion, followed by conducting autoclaving at 115° C. for 15 min. *Micrococcus luteus* with a 3% inoculum ($OD_{600}$=0.5 to 0.6) was inoculated into the mixture above. Shaker culture was conducted at 37° C., 150 rpm. After 72 h, 1 mL of a bacterial solution was placed in a 1.5 mL EP tube, centrifuged at 4,000 rpm for 5 min, and 1 μL of a lower layer precipitate was smeared on a glass slide, the slide glass was fixed with a liquid conductive adhesive on a pie-shaped battery, followed by spraying gold, and the battery was placed on a electron microscope stage to collect images after spraying gold (FIG. 9).

Experiment 3

1) A solution of 4% NaOH/7% Urea was prepared, 14 g/L microcrystalline cellulose was added to the solution, frozen at −20° C. for 24 h, and thawed at room temperature; when being heated to −14° C., the solution was in a state of an ice-water mixture. The stirring was conducted, and the solution was gradually clarified. After adjusting the pH value to 10 with HCl, the solution was filtered with gauze to collect a filtrate.

Figure 10:
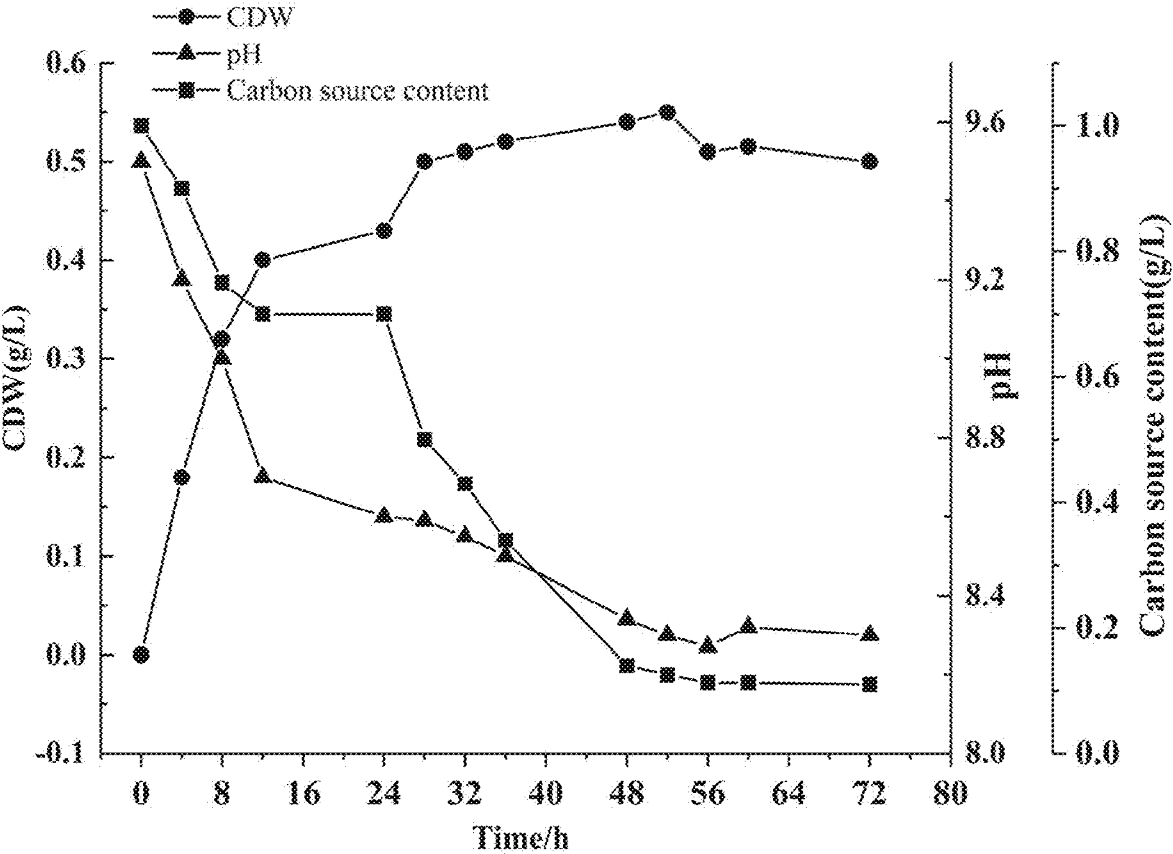
FIG. 10 shows changes of a dry cell weight, a pH value of medium, and a carbon source of medium of *Micrococcus luteus* after 72 h of culture with cellulose liquid obtained after NaOH/Urea system treatment of microcrystalline cellulose as the carbon source in an example of the present disclosure.

2) in the filtrate, $NH_4Cl$ (2 g/L), $MgSO_4$ (0.2 g/L), and NaCl (10 g/L) were added in proportion, followed by conducting autoclaving at 115° C. for 15 min. *Micrococcus luteus* with a 3% inoculum ($OD_{600}$=0.5 to 0.6) was inoculated into the mixture above. Shake fermentation culture was conducted at 37° C., 150 rpm for 72 h. A pH value, CDW and a cellulose content in the fermentation system (indirectly determined by a Fehling's reagent method) were measured every 8 h. It is found that with the increase of culture time, the pH value and glucose content are in a decreasing trend, while the CDW is in a continuous increasing trend, and an average CDW is about 0.52 g/L, as shown in FIG. 10.

Experiment 4

1) A solution of 4% NaOH/7% Urea was prepared, 14 g/L microcrystalline cellulose was added to the solution, frozen at −20° C. for 24 h, and thawed at room temperature; when being heated to −14° C., the solution was in a state of an ice-water mixture. The stirring was conducted, and the solution was gradually clarified. After adjusting the pH value to 10 with HCl, the solution was filtered with gauze to collect a filtrate.

2) in the filtrate, $NH_4Cl$ (2 g/L), $MgSO_4$ (0.2 g/L), and NaCl (10 g/L) were added in proportion, followed by conducting autoclaving at 115° C. for 15 min. *Micrococcus luteus* with a 3% inoculum ($OD_{600}$=0.5 to 0.6) was inoculated into the mixture above. Shake fermentation culture was conducted at 37° C., 150 rpm for 72 h. After 72 h, a culture was transferred to a 50 mL centrifuge tube, centrifuged at 12,000 rpm for 10 min, and a supernatant was discarded; a resulting precipitate was pre-frozen at −70° C. for 4 h, and then lyophilized overnight in a −60° C. vacuum lyophilizer.

3) Preparation of an esterification solution: 500 mL of anhydrous methanol (AR) was added with about 1 g/L benzoic acid and 3% (v/v) concentrated sulfuric acid (mass fraction 98%) carefully and slowly.

Figure 11A:
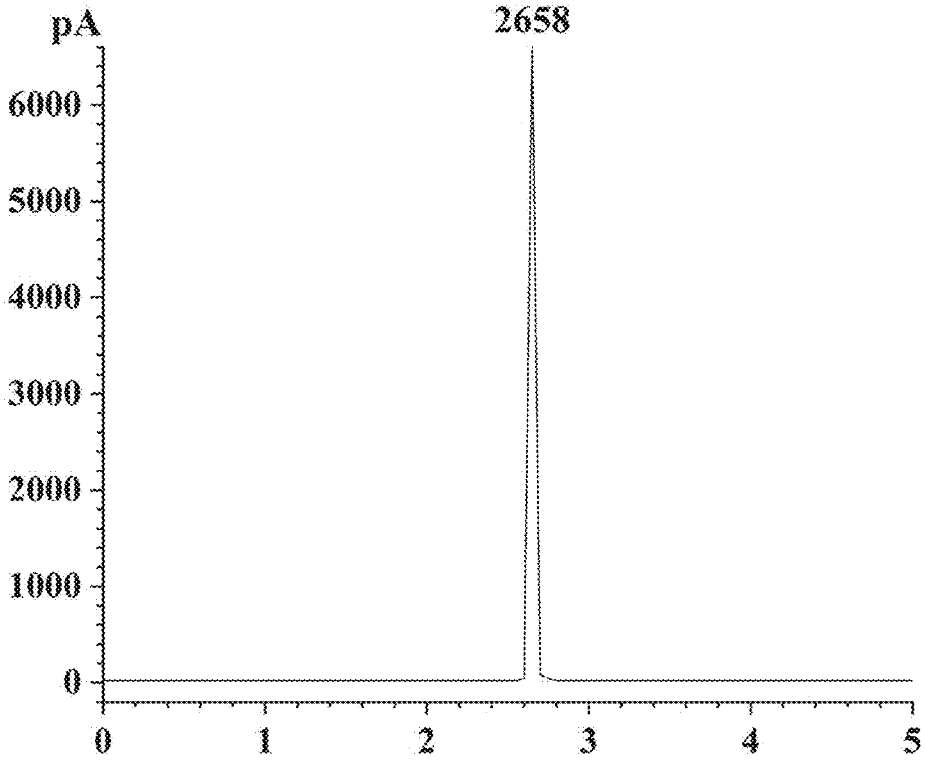
FIGS. 11A-11C show results of relevant PHA GC assays of *Micrococcus luteus* after 72 h of culture with cellulose liquid obtained after NaOH/Urea system treatment of microcrystalline cellulose as a carbon source in an example of the present disclosure.
Figure 11B:
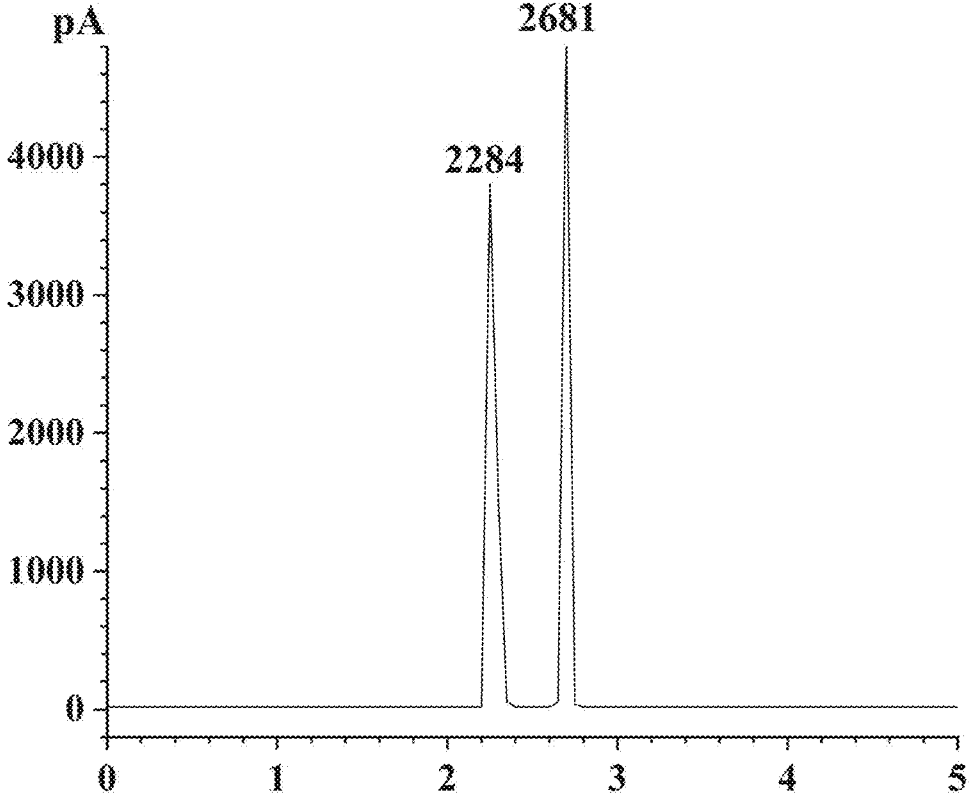
Figure 11C:
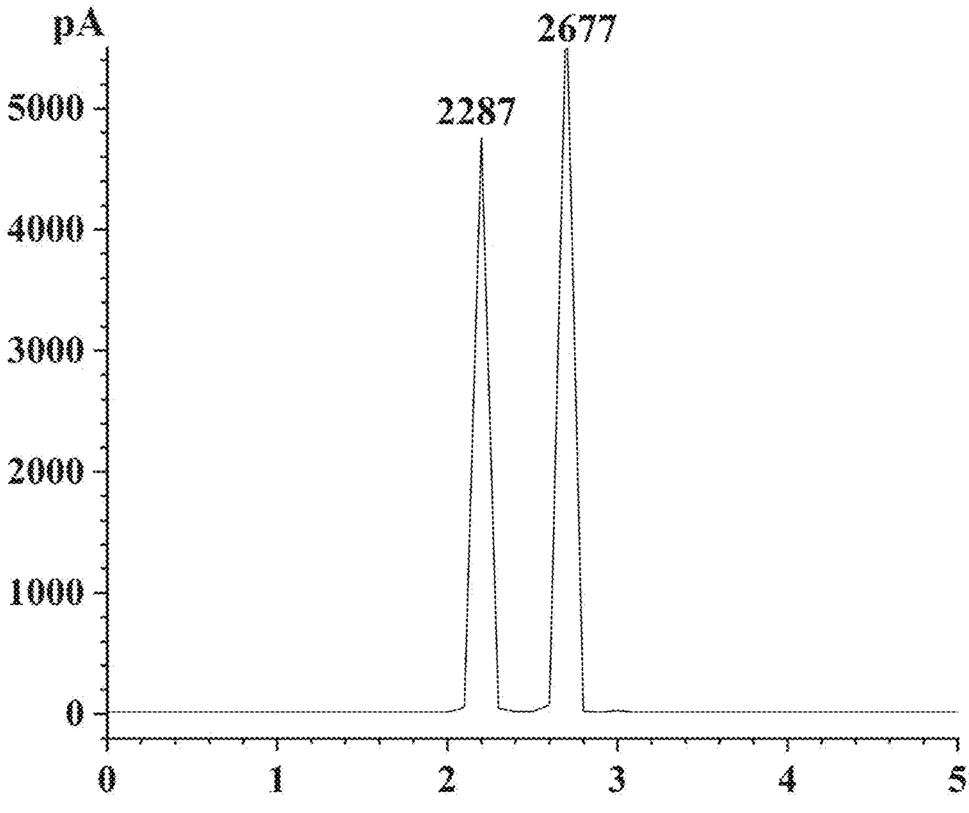

4) About 20 mg of freeze-dried cell samples were accurately weighed (0.0001 g) and placed in an esterification tube, and 2 mL of the chloroform (AR) and 2 mL of the esterification solution were added. About 10 mg of a standard polyhydroxy alkanoate (PHA) sample (PHB) was treated in the same way to prepare a chloroform solution of the standard sample. The esterification tube is sealed, shaken to mix evenly, followed by conducting esterification at a constant temperature of 100° C. for 4 h. After cooling to room temperature, 1 mL of $ddH_2O$ was added, shaken until completely mixed, and allowed to stand for about 30 min for layering. After the aqueous phase and the organic phase were completely separated, a lower layer solution (chloroform phase) was subjected to GC analysis to obtain results as shown in FIGS. 11A-11C. FIG. 11A shows a chromatographic result of a chloroform sample, where a first chromatographic peak is a chloroform solution with a retention time of 2.658 min; FIG. 11B shows a chromatographic result of a PHA standard sample after esterification, where a first chromatographic peak is 3HB with a retention time of 2.284 min, and a second chromatographic peak is chloroform with a retention time of 2.681 min; and FIG. 11C shows a chromatographic result of a freeze-dried strain of *Micrococcus luteus* after esterification, where a first peak has a retention time of 2.287 min, which is basically the same as that of a standard 3HB, and the calculated 3HB content is 28.19 wt %. This indicates that *Micrococcus luteus* can proliferate and accumulate PHA in the medium obtained by this method.

Experiment 5

1) Licorice straw was pulverized using a Chinese herbal medicine grinder, and sieved through a 30-mesh sieve to obtain a licorice straw powder. A solution of 4% NaOH/7% Urea was prepared, 10 g/L licorice straw powder was added to the solution, frozen at −20° C. for 24 h, and thawed at room temperature; when being heated to −14° C., the solution was in a state of an ice-water mixture. The stirring was conducted, and the solution was partially precipitated. After being adjusted to a pH value of 10 with HCl, the solution was filtered with gauze to collect a filtrate.

2) In the filtrate, $NH_4Cl$ (2 g/L), $MgSO_4$ (0.2 g/L), NaCl (10 g/L) were added in proportion, followed by conducting autoclaving at 115° C. for 15 min; *Micrococcus luteus* ($OD_{600}$=0.5 to 0.6) was inoculated with a 3% inoculum. It is found that the $OD_{600}$ is 0.31 at 0 h, and the $OD_{600}$ increases to 0.75 after 48 h. This proves that *Micrococcus luteus* can proliferate in this medium, indicating that the medium obtained by this method has a certain ability to culture microorganisms.

In this specification, descriptions of reference terms such as "one embodiment", "some embodiments", "an example", "a specific example" and "some examples" indicate that specific features, structures, materials or characteristics described in combination with the embodiment(s) or example(s) are included in at least one embodiment or example of the present disclosure. In this specification, schematic representation of the above terms is not necessarily directed to the same embodiment or example. Moreover, the specific features, structures, materials or characteristics described may be combined in a suitable manner in any one or more embodiments or examples. In addition, a person skilled in the art may combine different embodiments or examples described in this specification and characteristics of the different embodiments or examples without mutual contradiction.

Although the embodiments of the present disclosure have been illustrated and described above, it will be appreciated that the above embodiments are illustrative and should not be construed as limiting the scope of the present disclosure. Changes, modifications, substitutions and variations can be made to the above embodiments by a person of ordinary skill in the art within the scope of the present disclosure.

What is claimed is:

1. A method for preparing a carbon source for microbial medium, comprising:

1) mixing an ionic liquid and microcrystalline cellulose in a mass ratio of 5:3 to 10:1, wherein the ionic liquid is preheated at 70° C. to 90° C.;
2) mixing a mixed solution I obtained in step 1) and distilled water;
3) filtering a mixed solution II obtained in step 2), and collecting the filtrate; and
4) diluting the filtrate obtained in step 3) with distilled water to obtain the carbon source, wherein step 1) comprises:

i) heating the mixed solution of the ionic liquid and the cellulose to 100° C. to 140° C., stopping the heating, then stirring;
ii) heating the resulting mixed solution of step i) to 150° C. to 200° C., stopping the heating, then stirring; and
iii) repeating step ii) three times, wherein the ionic liquid comprises 1-butyl-3-methylimidazolium chloride.

2. The method according to claim 1, wherein the mixed solution I obtained in step 1) and the distilled water are mixed in a volume ratio of 1:2.

3. The method according to claim 1, further comprising: conducting fractionation on a diluted product I obtained in step 4) to obtain a carbon source without the ionic liquid and a first recycled ionic liquid.

4. The method according to claim 1, wherein the diluting is conducted according to a ratio of a mass of the ionic liquid to a diluting volume at 1 g:60 mL to 1 g:30 mL.

5. The method according to claim 3, wherein the diluting is conducted according to a ratio of a mass of the cellulose and a diluting volume at 1 g:50 mL to 1 g:30 mL.

6. The method according to claim 3, further comprising the following steps:

1) mixing the first recycled ionic liquid with the cellulose at a mass ratio of 5:3 to 10:1, wherein the first recycled ionic liquid is preheated at 100° C. to 140° C.;
2) heating the mixture I obtained in step 1) to 150° C. to 200° C., stopping the heating, then stirring;
3) repeating step 2) two times;
4) mixing a mixture II obtained in step 3) and distilled water in a volume ratio of 1:2;
5) filtering a product A obtained in step 4);
6) diluting a filtrate A obtained in step 5) with distilled water; and
7) conducting fractionation on a diluted product A obtained in step 6) to obtain the carbon source and a second recycled ionic liquid.

7. The method according to claim 3, wherein the fractionation is conducted using a rotary evaporator at a vacuum pressure of −0.070 Mpa to −0.095 Mpa and 40 rpm to 70 rpm, in a water bath at 20° C. to 50° C. and then 55° C. to 80° C.

* * * * *